United States Patent
Hobbs et al.

(10) Patent No.: US 9,173,704 B2
(45) Date of Patent: Nov. 3, 2015

(54) DEVICE AND METHOD FOR THE ABLATION OF FIBRIN SHEATH FORMATION ON A VENOUS CATHETER

(75) Inventors: Eamonn P. Hobbs, Queensbury, NY (US); William C. Hamilton, Jr., Queensbury, NY (US)

(73) Assignee: AngioDynamics, Inc., Latham, NY (US)

( * ) Notice: Subject to any disclaimer, the term of this patent is extended or adjusted under 35 U.S.C. 154(b) by 1271 days.

(21) Appl. No.: 12/488,070

(22) Filed: Jun. 19, 2009

(65) Prior Publication Data

US 2009/0318849 A1    Dec. 24, 2009

Related U.S. Application Data

(60) Provisional application No. 61/074,504, filed on Jun. 20, 2008.

(51) Int. Cl.
*A61B 18/12* (2006.01)
*A61B 18/14* (2006.01)
(Continued)

(52) U.S. Cl.
CPC ............ *A61B 18/1492* (2013.01); *A61N 1/327* (2013.01); *A61B 2018/0097* (2013.01); *A61B 2018/00357* (2013.01); *A61B 2018/00386* (2013.01); *A61B 2018/00613* (2013.01); *A61B 2018/00839* (2013.01)

(58) Field of Classification Search
CPC ........... A61B 2018/00571; A61B 2018/00613; A61B 2018/00773; A61B 2018/00839; A61B 18/1492; A61B 2018/00357; A61B 2018/0097; A61B 1/327; A61N 1/04; A61N 1/32; A61N 1/327
USPC ...................... 604/20, 22; 606/48, 50, 27–31; 607/101–102, 116
See application file for complete search history.

(56) References Cited

U.S. PATENT DOCUMENTS

| | | | |
|---|---|---|---|
| 1,653,819 | A | 12/1927 | Northcott et al. |
| 4,016,886 | A | 4/1977 | Doss |
| 4,226,246 | A | 10/1980 | Fragnet |

(Continued)

FOREIGN PATENT DOCUMENTS

| | | |
|---|---|---|
| DE | 863111 | 1/1953 |
| DE | 4000893 | 7/1991 |

(Continued)

OTHER PUBLICATIONS

Amasha, et al., Quantitative Assessment of Impedance Tomography for Temperature Measurements in Microwave Hyperthermia, *Clin. Phys. Physiol. Meas.*, 1998, Suppl. A, 49-53.

(Continued)

*Primary Examiner* — Jaymi Della
(74) *Attorney, Agent, or Firm* — Peter J. Flora

(57) ABSTRACT

An indwelling venous catheter and method capable of destroying undesirable cellular growth is provided. The catheter includes a shaft having at least one lumen and adapted to be placed inside a vein for long term use. A plurality of electrodes are positioned near a distal section of the shaft and are adapted to receive from a voltage generator a plurality of electrical pulses in an amount sufficient to cause destruction of cells in the undesirable cellular growth that have grown around the shaft. In one aspect of the invention, a probe is configured to be removably insertable into the at least one lumen and the electrodes are positioned near the distal section of the probe.

10 Claims, 12 Drawing Sheets

(51) Int. Cl.
*A61N 1/32* (2006.01)
*A61B 18/00* (2006.01)

(56) References Cited

U.S. PATENT DOCUMENTS

| | | | |
|---|---|---|---|
| 4,262,672 A | 4/1981 | Kief | |
| 4,407,943 A | 10/1983 | Cole et al. | |
| 4,810,963 A | 3/1989 | Blake-Coleman et al. | |
| 4,907,601 A | 3/1990 | Frick | |
| 4,946,793 A | 8/1990 | Marshall, III | |
| 5,019,034 A | 5/1991 | Weaver et al. | |
| 5,052,391 A | 10/1991 | Silberstone et al. | |
| 5,058,605 A | 10/1991 | Slovak | |
| 5,098,843 A | 3/1992 | Calvin | |
| 5,134,070 A | 7/1992 | Casnig | |
| 5,173,158 A | 12/1992 | Schmukler | |
| 5,193,537 A | 3/1993 | Freeman | |
| 5,273,525 A | 12/1993 | Hofmann | |
| 5,283,194 A | 2/1994 | Schmukler | |
| 5,318,563 A | 6/1994 | Malis et al. | |
| 5,328,451 A | 7/1994 | Davis et al. | |
| 5,389,069 A | 2/1995 | Weaver | |
| 5,403,311 A | 4/1995 | Abele et al. | |
| 5,425,752 A | 6/1995 | Vu'Nguyen | |
| 5,439,440 A | 8/1995 | Hofmann | |
| 5,458,625 A | 10/1995 | Kendall | |
| 5,533,999 A | 7/1996 | Hood et al. | |
| 5,536,240 A | 7/1996 | Edwards et al. | |
| 5,575,811 A | 11/1996 | Reid et al. | |
| 5,626,146 A | 5/1997 | Barber et al. | |
| 5,634,899 A | 6/1997 | Shapland et al. | |
| 5,643,197 A * | 7/1997 | Brucker et al. | 604/20 |
| 5,674,267 A | 10/1997 | Mir et al. | |
| 5,702,359 A | 12/1997 | Hofmann | |
| 5,720,921 A | 2/1998 | Meserol | |
| 5,778,894 A | 7/1998 | Dorogi et al. | |
| 5,782,882 A | 7/1998 | Lerman et al. | |
| 5,800,378 A | 9/1998 | Edwards et al. | |
| 5,810,762 A | 9/1998 | Hofmann | |
| 5,836,905 A | 11/1998 | Lemelson et al. | |
| 5,843,026 A | 12/1998 | Edwards et al. | |
| 5,873,849 A | 2/1999 | Bernard | |
| 5,919,142 A | 7/1999 | Boone et al. | |
| 5,947,889 A | 9/1999 | Hehrlein | |
| 5,983,131 A | 11/1999 | Weaver et al. | |
| 5,991,697 A | 11/1999 | Nelson et al. | |
| 5,999,847 A | 12/1999 | Elstrom | |
| 6,009,347 A | 12/1999 | Hofmann | |
| 6,010,613 A | 1/2000 | Walters et al. | |
| 6,016,452 A | 1/2000 | Kasevich | |
| 6,041,252 A | 3/2000 | Walker et al. | |
| 6,055,453 A | 4/2000 | Hofmann et al. | |
| 6,068,650 A | 5/2000 | Nanda et al. | |
| 6,085,115 A | 7/2000 | Weaver et al. | |
| 6,090,106 A | 7/2000 | Goble et al. | |
| 6,102,885 A | 8/2000 | Bass | |
| 6,106,521 A | 8/2000 | Blewett et al. | |
| 6,109,270 A | 8/2000 | Mah et al. | |
| 6,122,599 A | 9/2000 | Mehta | |
| 6,132,419 A | 10/2000 | Hofmann | |
| 6,159,163 A | 12/2000 | Strauss et al. | |
| 6,208,893 B1 | 3/2001 | Hofmann | |
| 6,210,402 B1 | 4/2001 | Olsen et al. | |
| 6,212,433 B1 | 4/2001 | Behl | |
| 6,216,034 B1 | 4/2001 | Hofmann | |
| 6,219,577 B1 | 4/2001 | Brown et al. | |
| 6,241,702 B1 | 6/2001 | Lundquist et al. | |
| 6,261,831 B1 | 7/2001 | Agee | |
| 6,278,895 B1 | 8/2001 | Bernard | |
| 6,300,108 B1 | 10/2001 | Rubinsky | |
| 6,326,177 B1 | 12/2001 | Schoenbach et al. | |
| 6,347,247 B1 | 2/2002 | Dev et al. | |
| 6,349,233 B1 | 2/2002 | Adams | |
| 6,351,674 B2 | 2/2002 | Silverstone | |
| 6,387,671 B1 | 5/2002 | Rubinsky et al. | |
| 6,403,348 B1 | 6/2002 | Rubinsky et al. | |
| 6,419,674 B1 * | 7/2002 | Bowser et al. | 606/45 |
| 6,470,211 B1 | 10/2002 | Ideker et al. | |
| 6,482,619 B1 | 11/2002 | Rubinsky et al. | |
| 6,493,592 B1 | 12/2002 | Leonard et al. | |
| 6,500,173 B2 | 12/2002 | Underwood et al. | |
| 6,526,320 B2 | 2/2003 | Mitchell | |
| 6,562,604 B2 | 5/2003 | Rubinsky et al. | |
| 6,607,529 B1 | 8/2003 | Jones et al. | |
| 6,611,706 B2 | 8/2003 | Avrahami et al. | |
| 6,613,211 B1 | 9/2003 | McCormick et al. | |
| 6,627,421 B1 | 9/2003 | Unger et al. | |
| 6,653,091 B1 | 11/2003 | Dunn et al. | |
| 6,669,691 B1 | 12/2003 | Taimisto | |
| 6,692,493 B2 | 2/2004 | McGovern et al. | |
| 6,697,669 B2 | 2/2004 | Dev et al. | |
| 6,697,670 B2 | 2/2004 | Chornenky et al. | |
| 6,702,808 B1 | 3/2004 | Kreindel | |
| 6,795,728 B2 | 9/2004 | Chornenky et al. | |
| 6,801,804 B2 | 10/2004 | Miller et al. | |
| 6,865,416 B2 | 3/2005 | Dev et al. | |
| 6,892,099 B2 | 5/2005 | Jaafar et al. | |
| 6,912,417 B1 | 6/2005 | Bernard et al. | |
| 6,927,049 B2 | 8/2005 | Rubinsky et al. | |
| 6,962,587 B2 | 11/2005 | Johnson et al. | |
| 6,972,014 B2 | 12/2005 | Eum et al. | |
| 6,994,706 B2 | 2/2006 | Chornenky et al. | |
| 7,053,063 B2 | 5/2006 | Rubinsky et al. | |
| 7,063,698 B2 | 6/2006 | Whayne et al. | |
| 7,130,697 B2 | 10/2006 | Chornenky et al. | |
| 7,211,083 B2 | 5/2007 | Chornenky et al. | |
| 7,267,676 B2 | 9/2007 | Chornenky et al. | |
| 2001/0044596 A1 * | 11/2001 | Jaafar | 604/103.01 |
| 2002/0010491 A1 | 1/2002 | Schoenbach | |
| 2002/0055731 A1 | 5/2002 | Atala et al. | |
| 2002/0077676 A1 | 6/2002 | Schroeppel et al. | |
| 2002/0099323 A1 | 7/2002 | Dev et al. | |
| 2002/0138117 A1 | 9/2002 | Son | |
| 2002/0193831 A1 | 12/2002 | Smith, III | |
| 2003/0009110 A1 | 1/2003 | Tu et al. | |
| 2003/0060856 A1 | 3/2003 | Chornenky et al. | |
| 2003/0088189 A1 | 5/2003 | Tu et al. | |
| 2003/0109871 A1 * | 6/2003 | Johnson et al. | 606/42 |
| 2003/0130711 A1 | 7/2003 | Pearson et al. | |
| 2003/0170898 A1 | 9/2003 | Gundersen et al. | |
| 2003/0208200 A1 | 11/2003 | Palanker et al. | |
| 2003/0225360 A1 | 12/2003 | Eppstein et al. | |
| 2004/0019371 A1 | 1/2004 | Jaafar et al. | |
| 2004/0059389 A1 | 3/2004 | Chornenky et al. | |
| 2004/0116965 A1 * | 6/2004 | Falkenberg | 607/5 |
| 2004/0146877 A1 | 7/2004 | Diss et al. | |
| 2004/0153057 A1 | 8/2004 | Davison | |
| 2004/0243107 A1 | 12/2004 | Mackoviak et al. | |
| 2004/0267189 A1 | 12/2004 | Mavor et al. | |
| 2005/0043726 A1 | 2/2005 | McHale et al. | |
| 2005/0049541 A1 | 3/2005 | Behar et al. | |
| 2005/0143817 A1 * | 6/2005 | Hunter et al. | 623/11.11 |
| 2005/0165393 A1 | 7/2005 | Eppstein | |
| 2005/0171523 A1 | 8/2005 | Rubinsky et al. | |
| 2005/0171574 A1 | 8/2005 | Rubinsky et al. | |
| 2005/0182462 A1 | 8/2005 | Chornenky et al. | |
| 2005/0197619 A1 * | 9/2005 | Rule et al. | 604/22 |
| 2005/0261672 A1 | 11/2005 | Deem et al. | |
| 2005/0288730 A1 | 12/2005 | Deem et al. | |
| 2006/0015147 A1 | 1/2006 | Persson et al. | |
| 2006/0025760 A1 | 2/2006 | Podhajsky | |
| 2006/0079883 A1 | 4/2006 | Elmouelhi et al. | |
| 2006/0121610 A1 | 6/2006 | Rubinsky et al. | |
| 2006/0212078 A1 | 9/2006 | Demarais et al. | |
| 2006/0217703 A1 | 9/2006 | Chornenky et al. | |
| 2006/0264752 A1 | 11/2006 | Rubinsky et al. | |
| 2006/0293730 A1 * | 12/2006 | Rubinsky et al. | 607/98 |
| 2007/0043345 A1 | 2/2007 | Davalos et al. | |
| 2007/0060989 A1 * | 3/2007 | Deem et al. | 607/99 |
| 2007/0078391 A1 | 4/2007 | Wortley et al. | |
| 2007/0118069 A1 | 5/2007 | Persson et al. | |
| 2007/0239099 A1 * | 10/2007 | Goldfarb et al. | 604/20 |
| 2008/0052786 A1 | 2/2008 | Lin et al. | |

(56) References Cited

U.S. PATENT DOCUMENTS

FOREIGN PATENT DOCUMENTS

| EP | 0378132 | 7/1990 |
|---|---|---|
| EP | 0935482 | 5/2005 |
| WO | 9639531 | 12/1996 |
| WO | 0020554 | 4/2000 |
| WO | 0107583 | 2/2001 |
| WO | 0107584 | 2/2001 |
| WO | 0107585 | 2/2001 |
| WO | 0181533 | 11/2001 |
| WO | 04037341 | 5/2004 |
| WO | 2005065284 A2 | 7/2005 |

OTHER PUBLICATIONS

Andreason, Electroporation as a Technique for the Transfer of Macromolecules into Mammalian Cell Lines, *J. Tiss. Cult. Meth.*, 15:56-62, 1993.
Baker, et al., Calcium-Dependent Exocytosis in Bovine Adrenal Medullary Cells with Leaky Plasma Membranes, *Nature*, vol. 276, pp. 620-622, 1978.
Barber, Electrical Impedance Tomography Applied Potential Tomography, Advances in Biomedical Engineering, Beneken and Thevenin, eds., IOS Press, 1993.
Beebe, S.J., et al., Nanosecond pulsed electric field (nsPEF) effects on cells and tissues: apoptosis induction and tumor growth inhibition. PPPS-2001 Pulsed Power Plasma Science 2001, 28$^{th}$ IEEE International Conference on Plasma Science and 13$^{th}$ IEEE International Pulsed Conference, Digest of Technical Papers (Cat. No. 01CH37251). IEEE, Part vol. 1, 2001, pp. 211-215, vol. I, Piscataway, NJ, USA.
Blad, et al., Impedance Spectra of Tumour Tissue in Comparison with Normal Tissue; a Possible Clinical Application for Electrical Impedance Tomography, *Physiol. Meas.* 17 (1996) A105-A115.
Bown, S.G., Phototherapy of tumors. *World J. Surgery*, 1983. 7: p. 700-9.
BPH Management Strategies: Improving Patient Satisfaction, *Urology Times*, May 2001, vol. 29, Supplement 1.
Brown, et al., Blood Flow Imaging Using Electrical Impedance Tomography, *Clin. Phys. Physiol. Meas.*, 1992, vol. 13, Suppl. A, 175-179.
Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.
Coates, C.W., et al., "The Electrical Discharge of the Electric Eel, Electrophorous Electricus," Zoologica, 1937, 22(1), pp. 1-32.
Cook, et al., ACT3: A High-Speed, High-Precision Electrical Impedance Tomograph, *IEEE Transactions on Biomedical Engineering*, vol. 41, No. 8, Aug. 1994.
Cowley, Good News for Boomers, *Newsweek*, Dec. 30, 1996/Jan. 6, 1997.
Cox, et al., Surgical Treatment of Atrial Fibrillation: A Review, *Europace* (2004) 5, S20-S-29.
Crowley, Electrical Breakdown of Biomolecular Lipid Membranes as an Electromechanical Instability, *Biophysical Journal*, vol. 13, pp. 711-724, 1973.
Davalos, et al., Tissue Ablation with Irreversible Electroporation, *Annals of Biomedical Engineering*, vol. 33, No. 2, Feb. 2005.
Davalos, et al., Theoretical Analysis of the Thermal Effects During in Vivo Tissue Electroporation, Bioelectrochemistry, vol. 61, pp. 99-107, 2003.
Davalos, et al., A Feasibility Study for Electrical Impedance Tomography as a Means to Monitor T issue Electroporation for Molecular Medicine, *IEEE Transactions on Biomedical Engineering*, vol. 49, No. 4, Apr. 2002.
Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002.
Dean, Nonviral Gene Transfer to Skeletal, Smooth, and Cardiac Muscle in Living Animals, *Am J. Physiol Cell Physiol* 289: 233-245, 2005.
Dev, et al., Sustained Local Delivery of Heparin to the Rabbit Arterial Wall with an Electroporation Catheter, *Catheterization and Cardiovascular Diagnosis*, Nov. 1998, vol. 45, No. 3, pp. 337-343.
Dev, et al., Medical Applications of Electroporation, *IEEE Transactions of Plasma Science*, vol. 28, No. 1, pp. 206-223, Feb. 2000.
Duraiswami, et al., Boundary Element Techniques for Efficient 2-D and 3-D Electrical Impedance Tomography, *Chemical Engineering Science*, vol. 52, No. 13, pp. 2185-2196, 1997.
Duraiswami, et al., Efficient 2D and 3D Electrical Impedance Tomography Using Dual Reciprocity Boundary Element Techniques, *Engineering Analysis with Boundary Elements* 22, (1998) 13-31.
Duraiswami, et al., Solution of Electrical Impedance Tomography Equations Using Boundary Element Methods, *Boundary Element Technology XII*, 1997, pp. 226-237.
Edd, J., et al., In-Vivo Results of a New Focal Tissue Ablation Technique: Irreversible Electroporaton, *IEEE Trans. Biomed. Eng.* 53 (2006) p. 1409-1415.
Erez, et al., Controlled Destruction and Temperature Distributions in Biological Tissues Subjected to Monoactive Electrocoagulation, *Transactions of the ASME: Journal of Mechanical Design*, vol. 102, Feb. 1980.
Foster, R.S., et al., High-intensity focused ultrasound in the treatment of prostatic disease. *Eur. Urol.*, 1993. 23: 44-7).
Fox, et al., Sampling Conductivity Images via MCMC, Mathematics Department, Auckland University, New Zealand, May 1997.
Gauger, et al., A Study of Dielectric Membrane Breakdown in the Fucus Egg, *J. Membrane Biol.*, vol. 48, No. 3, pp. 249-264, 1979.
Gehl, et al., In Vivo Electroporation of Skeletal Muscle: Threshold, Efficacy and Relation to Electric Field Distribution, *Biochimica et Biphysica Acta* 1428, 1999, pp. 233-240.
Gençer, et al., Electrical Impedance Tomography: Induced-Current Imaging Achieved with a Multiple Coil System, *IEEE Transactions on Biomedical Engineering*, vol. 43, No. 2, Feb. 1996.
Gilbert, et al., Novel Electrode Designs for Electrochemotherapy, *Biochimica et Biophysica Acta* 1334, 1997, pp. 9-14.
Gilbert, et al., The Use of Ultrasound Imaging for Monitoring Cryosurgery, Proceedings 6$^{th}$ Annual Conference, IEEE Engineering in Medicine and Biology, 107-111, 1984.
Glidewell, et al., The Use of Magnetic Resonance Imaging Data and the Inclusion of Anisotropic Regions in Electrical Impedance Tomography, *Biomed, Sci. Instrum.* 1993; 29: 251-7.
Gothelf, et al., Electrochemotherapy: Results of Cancer Treatment Using Enhanced Delivery of Bleomycin by Electroporation, *Cancer Treatment Reviews* 2003: 29: 371-387.
Griffiths, et al., A Dual-Frequency Electrical Impedance Tomography System, *Phys. Med. Biol.*, 1989, vol. 34, No. 10, pp. 1465-1476.
Griffiths, The Importance of Phase Measurement in Electrical Impedance Tomography, *Phys. Med. Biol.*, 1987, vol. 32, No. 11, pp. 1435-1444.
Griffiths, Tissue Spectroscopy with Electrical Impedance Tomography: Computer Simulations, *IEEE Transactions on Biomedical Engineering*, vol. 42, No. 9, Sep. 1995.
Gumerov, et al., The Dipole Approximation Method and Its Coupling with the Regular Boundary Element Method for Efficient Electrical Impedance Tomography, *Boundary Element Technology XIII*, 1999.
Hapala, Breaking the Barrier: Methods for Reversible Permeabilization of Cellular Membranes, *Critical Reviews in Biotechnology*, 17(2): 105-122, 1997.
Heller, et al., Clinical Applications of Electrochemotherapy, *Advanced Drug Delivery Reviews*, vol. 35, pp. 119-129, 1999.
Ho, et al., Electroporation of Cell Membranes: A Review, *Critical Reviews in Biotechnology*, 16(4): 349-362, 1996.
Holder, et al., Assessment and Calibration of a Low-Frequency System for Electrical Impedance Tomography (EIT), Optimized for Use in Imaging Brain Function in Ambulant Human Subjects, *Annals of the New York Academy of Science*, vol. 873, Issue 1, Electrical BI, pp. 512-519, 1999.

(56) References Cited

OTHER PUBLICATIONS

Huang, et al., Micro-Electroporation: Improving the Efficiency and Understanding of Electrical Permeabilization of Cells, *Biomedical Microdevices*, vol. 2, pp. 145-150, 1999.

Hughes, et al., An Analysis of Studies Comparing Electrical Impedance Tomography with X-Ray Videofluoroscopy in the Assessment of Swallowing, *Physiol. Meas.* 15, 1994, pp. A199-A209.

Issa, et al., The TUNA Procedure for BPH: Review of the Technology: The TUNA Procedure for BPH: Basic Procedure and Clinical Results, Reprinted from *Infections in Urology*, Jul./Aug. 1998 and Sep./Oct. 1998.

Ivanuša, et al., MRI Macromolecular Contrast Agents as Indicators of Changed Tumor Blood Flow, *Radiol. Oncol.* 2001; 35(2): 139-47.

Jaroszeski, et al., In Vivo Gene Delivery by Electroporation, *Advanced Drug Delivery Review*, vol. 35, pp. 131-137, 1999.

Kinosita, et al., Hemolysis of Human Erythrocytes by a Transient Electric Field, *Proc. Natl. Acad. Sci. USA*, vol. 74, No. 5, pp. 1923-1927, 1977.

Liu, et al., Measurement of Pharyngeal Transit Time by Electrical Impedance Tomography, *Clin. Phys. Physiol. Meas.*, 1992, vol. 13, Suppl. A, pp. 197-200.

Lundqvist, et al., Altering the Biochemical State of Individual Cultured Cells and Organelles with Ultramicroelectrodes, *Proc. Natl. Acad. Sci. USA*, vol. 95, pp. 10356-10360, Sep. 1998.

Lurquin, Gene Transfer by Electroporation, *Molecular Biotechnology*, vol. 7, 1997.

Lynn, et al., A New Method for the Generation and Use of Focused Ultrasound in Experimental Biology, *The Journal of General Physiology*, vol. 26, 179-193, 1942.

Miklavčič, et al., A Validated Model of an in Vivo Electric Field Distribution in Tissues for Electrochemotherapy and for DNA Electrotransfer for Gene Therapy, *Biochimica et Biophysica Acta* 1523 (2000), pp. 73-83.

Miklavčič, et al., The Importance of Electric Field Distribution for Effective in Vivo Electroporation of Tissues, *Biophysical Journal*, vol. 74, May 1998, pp. 2152-2158.

Miller, L., et al., Cancer cells ablation with irreversible electroporation, *Technology in Cancer Research and Treatment* 4 (2005) 699-706.

Mir, Therapeutic Perspectives of in Vivo Cell Electropermeabilization, *Bioelectrochemistry*, vol. 53, pp. 1-10, 2000.

Mir, L.M., et al., Electric Pulse-Mediated Gene Delivery to Various Animal Tissues, in Advances in Genetics, Academic Press, 2005, p. 83-114.

Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.

Mir, et al., Effective Treatment of Cutaneous and Subcutaneous Malignant Tumours by Electrochemotherapy, *British Journal of Cancer*, vol. 77, No. 12, pp. 2336-2342, 1998.

Mir, et al., Electrochemotherapy Potentiation of Antitumour Effect of Bleomycin by Local Electric Pulses, European Journal of Cancer, vol. 27, No. 1, pp. 68-72, 1991.

Mir, et al., Electrochemotherapy, a Novel Antitumor Treatment: First Clinical Trial, *C.R. Acad. Sci. Paris*, Ser. III, vol. 313, pp. 613-618, 1991.

Narayan, et al., Establishment and Characterization of a Human Primary Prostatic Adenocarcinoma Cell Line (ND-1), *The Journal of Urology*, vol. 148, 1600-1604, Nov. 1992.

Naslund, Michael J., Transurethral Needle Ablation of the Prostate, *Urology*, vol. 50, No. 2, Aug. 1997.

Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5,2001.

Neumann, et al., Gene Transfer into Mouse Lyoma Cells by Electroporation in High Electric Fields, *J. Embo.*, vol. 1, No. 7, pp. 841-845, 1982.

Neumann, et al., Permeability Changes Induced by Electric Impulses in Vesicular Membranes, *J. Membrane Biol.*, vol. 10, pp. 279-290, 1972.

Okino, et al., Effects of High-Voltage Electrical Impulse and an Anticancer Drug on in Vivo Growing Tumors, *Japanese Journal of Cancer Research*, vol. 78, pp. 1319-1321, 1987.

Onik, et al., Sonographic Monitoring of Hepatic Cryosurgery in an Experimental Animal Model, *AJR American J. of Roentgenology*, vol. 144, pp. 1043-1047, May 1985.

Onik, et al., Ultrasonic Characteristics of Frozen Liver, *Cryobiology*, vol. 21, pp. 321-328, 1984.

Organ, L.W., Electrophysiological principles of radiofrequency lesion making, *Apply. Neurophysiol.*, 1976. 39: p. 69-76.

Piñero, et al., Apoptotic and Necrotic Cell Death Are Both Induced by Electroporation in HL60 Human Promyeloid Leukaemia Cells, *Apoptosis*, Vol, 2, No. 3, 330-336, Aug. 1997.

Precision Office TUNA System, When Patient Satisfaction is Your Goal.

Rols, M.P., et al., Highly Efficient Transfection of Mammalian Cells by Electric Field Pulses: Application to Large Volumes of Cell Culture by Using a Flow System, *Eur. J. Biochem.* 1992, 206, pp. 115-121.

Rubinsky, B., ed, Cryosurgery. *Annu Rev. Biomed.* Eng. vol. 2 2000. 157-187.

Schmukler, Impedance Spectroscopy of Biological Cells, downloaded from IEEE Xplore website.

Sersa, et al., Reduced Blood Flow and Oxygenation in SA-1 Tumours after Electrochemotherapy with Cisplatin, *British Journal of Cancer*, 87, 1047-1054, 2002.

Sersa, et al., Tumour Blood Flow Modifying Effects of Electrochemotherapy: A Potential Vascular Targeted Mechanism, *Radiol. Oncol.*, 37(1): 43-8, 2003.

Sharma, et al., Poloxamer 188 Decreases Susceptibility of Artificial Lipid Membranes to Electroporation, *Biophysical Journal*, vol. 71, No. 6, pp. 3229-3241, Dec. 1996.

Shiina, S., et al, Percutaneous ethanol injection therapy for hepatocellular carcinoma: results in 146 patients. *AJR*, 1993, 160: p. 1023-8.

Thompson, et al., to determine whether the temperature of 2% lignocaine gel affects the initial discomfort which may be associated with its instillation into the male urethra, *BJU International* (1999), 84, 1035-1037.

TUNA—Suggested Local Anesthesia Guidelines.

VIDAMED, Inc., Transurethral Needle Ablation (TUNA): Highlights from Worldwide Clinical Studies, Vidamed's Office TUNA System.

Weaver, Electroporation: A General Phenomenon for Manipulating Cells and Tissues, *Journal of Cellular Biochemistry*, 51: 426-435, 1993.

Weaver, et al., Theory of Electroporation: A Review, *Bioelectrochemistry and Bioenergetics*, vol. 41, pp. 136-160, 1996.

Zimmermann, et al., Dielectric Breakdown of Cell Membranes, *Biophysical Journal*, vol. 14, No. 11, pp. 881-899, 1974.

Zlotta, et al., Possible Mechanisms of Action of Transurethral Needle Ablation of the Prostate on Benign Prostatic Hyperplasia Symptoms: a Neurohistochemical Study, Reprinted from *Journal of Urology*, vol. 157, No. 3, Mar. 1997, pp. 894-899.

Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.

Savader, et al., "Treatment of Hemodialysis Catheter-associated Fibrin Sheaths by rt-PA Infusion: Critical Analysis of 124 Procedures," J Vasc Intery Radiol 2001; 12:711-715.

\* cited by examiner

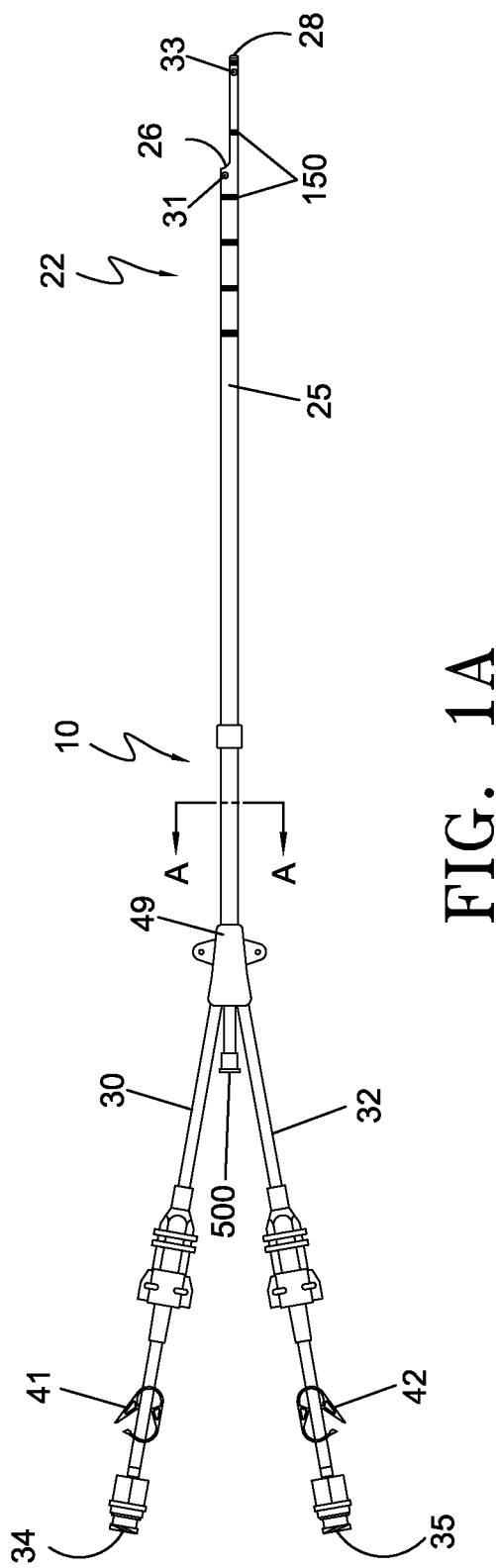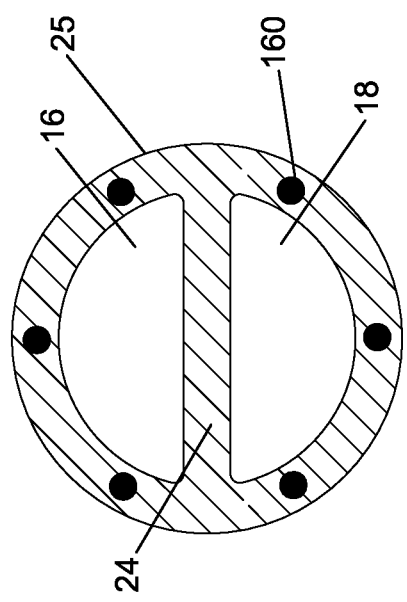
FIG. 1A
FIG. 1B

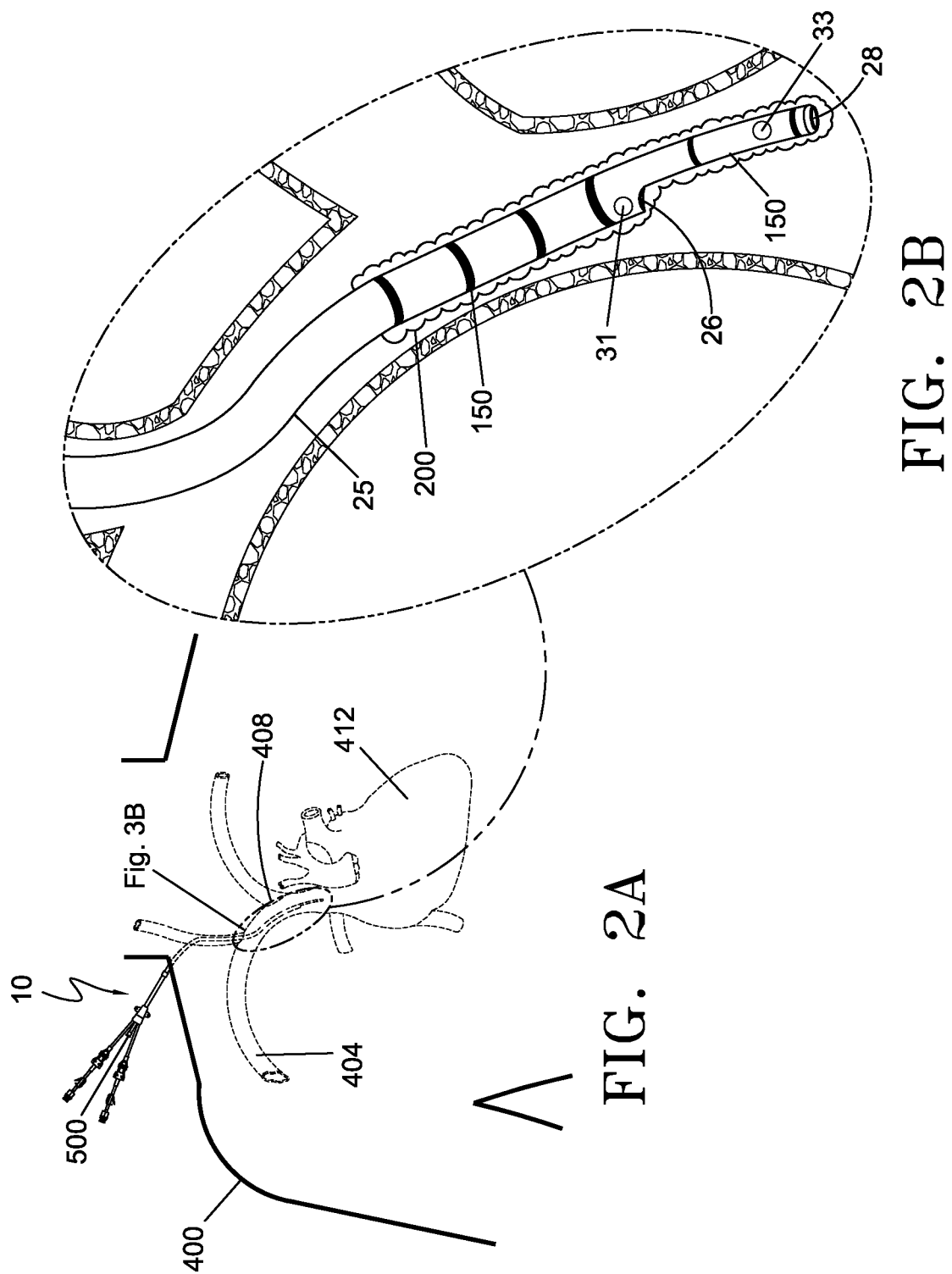

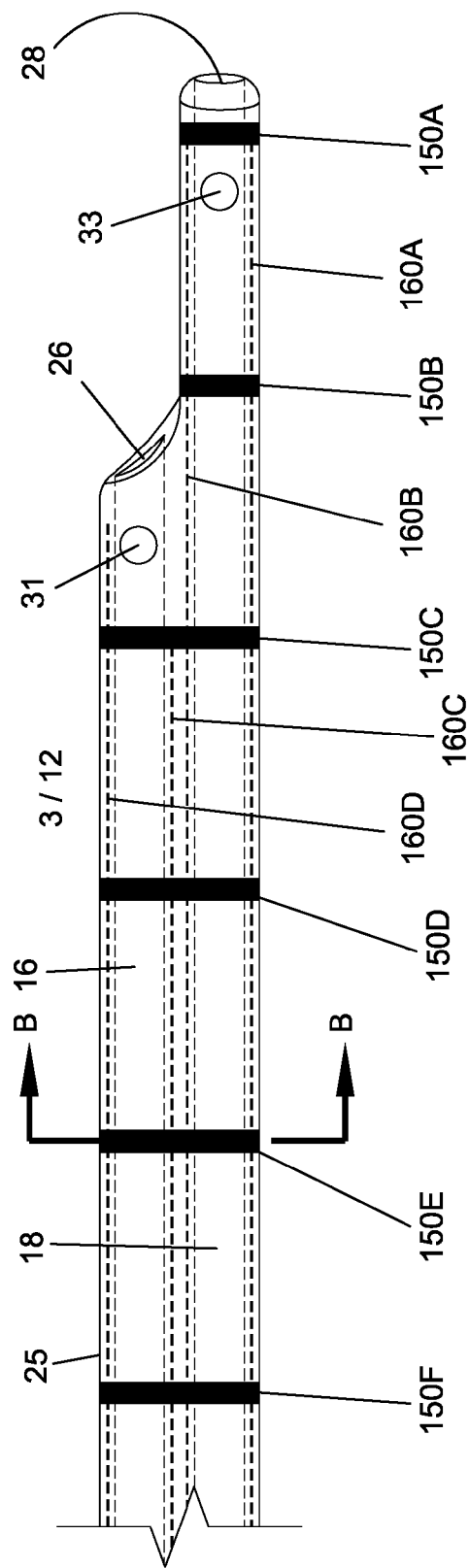
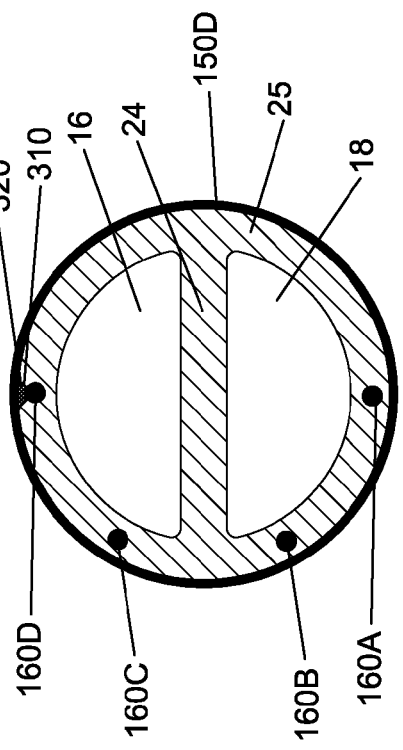
FIG. 3A
FIG. 3B

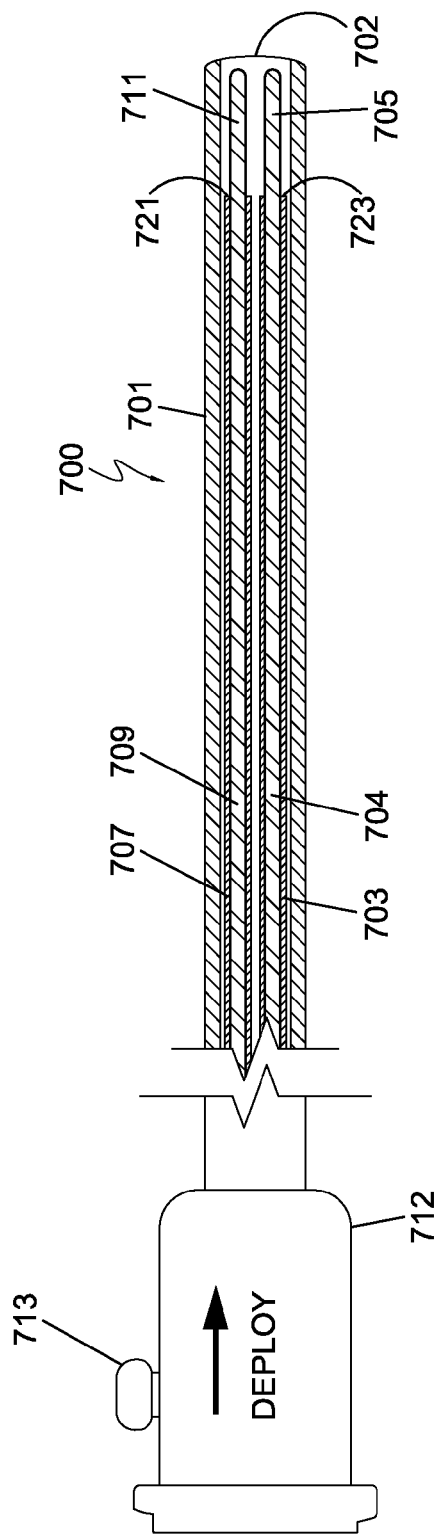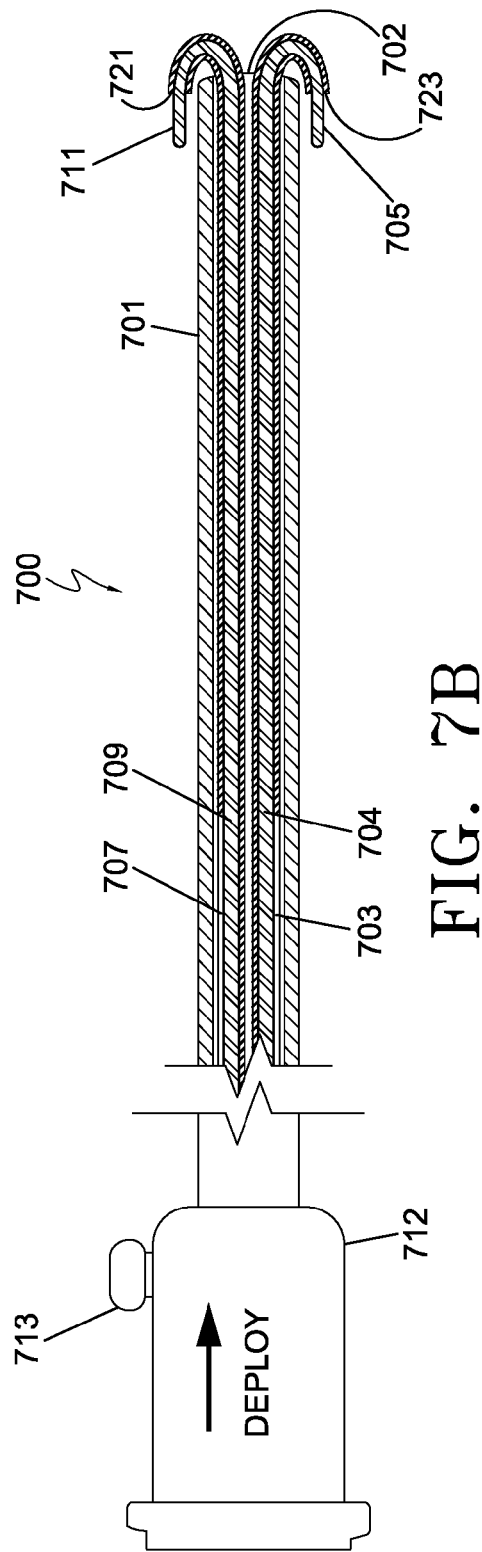

DEVICE AND METHOD FOR THE ABLATION OF FIBRIN SHEATH FORMATION ON A VENOUS CATHETER

CROSS REFERENCE TO RELATED APPLICATIONS

This application claims the benefit of priority under 35 U.S.C. Section 119(e) to U.S. Provisional Application Ser. No. 61/074,504, filed Jun. 20, 2008, entitled "Device And Method For The Ablation Of Fibrin Sheath Formation On A Venous Catheter Using Electroporation", which is fully incorporated by reference herein.

FIELD OF THE INVENTION

The present invention relates to a medical device and method for the destruction of undesirable cellular growth on a venous catheter, such as fibrin sheath formation and/or infectious cells, by delivering a plurality of electrical pulses.

BACKGROUND OF THE INVENTION

Catheters, and more particularly, venous access catheters have many very important medical applications. For example, if a patient requires long-term dialysis therapy, a venous access catheter, such as a chronic dialysis catheter, will be implanted in a patient's body. Chronic dialysis catheters typically contain a polyester cuff that is tunneled beneath the skin approximately 3-8 cm and helps to anchor the dialysis catheter to the body. The chronic dialysis catheter is connected to a dialysis machine when the patient is treated. Hemodialysis is a method for removing waste products such as potassium and urea from the blood, such as in the case of renal failure. During hemodialysis, waste products that have accumulated in the blood because of kidney failure are transferred via mass transfer from the blood across a semi permeable dialysis membrane to a balanced salt solution.

In another example, a venous catheter can be used in combination with an implanted port. A port can be implanted in patients that require frequent access to the venous blood, such as chemotherapy patients. An implanted port includes attachment means for fluidly connecting a catheter. The port is implanted in a surgically created pocket within the patient's body and has a reservoir for delivering fluids through the catheter. One end of the catheter is connected to the port, and the other end terminates in a vein near the patient's heart.

Another example of a long-term venous access catheter is a peripherally inserted central catheter, also known as a PICC line. PICC lines are placed in patients requiring long-term access for the purpose of blood sampling and infusion of therapeutic agents including chemotherapeutic drugs.

Notwithstanding the importance of venous catheters, one problem that is associated with their use is the undesired formation of fibrin sheaths along the catheter wall. See, for example, Savader, et al., *Treatment of Hemodialysis Catheter-associated Fibrin Sheaths by rt-PA Infusion: Critical Analysis of* 124 *Procedures*, J. Vasc. Interv. Radiol. 2001; 12:711-715. Fibrin sheath formation is an insidious problem that can plague essentially all central venous catheters. It has been reported that fibrin sheath formation occurred as early as 24 hours after catheter placement and that this phenomenon was seen on 100% of central venous catheters in 55 patients at the time of autopsy.

The growth of a fibrin sheath along a catheter shaft can prevent high flow rates, adversely affect blood sampling and infusion of chemotherapeutic drugs, and provide an environment in which bacteria can grow, which may result in infections. Despite fibrin sheath build up, infused fluids may still enter the blood circulation, but when negative pressure is applied, the fibrin sheath can be drawn into the catheter, occluding its tip, thereby preventing aspiration. Complete encasement of the catheter tip in a fibrin sheath may cause persistent withdrawal occlusion. This can lead to extravasation of fluid where fluid enters the catheter to flow into the fibrin sheath, backtracks along the outside of the catheter, and exits out of the venous entry point and into the tissue. The presence of a fibrin sheath on the catheter shaft may also result in difficulty removing the venous catheter, particularly PICC lines, from the patient.

Often patients who need prolonged intravenous regimens have compromised peripheral venous access and thus venous catheters are often the only means available for the delivery of necessary treatment. Therefore, such venous catheters should be configured to remain in a patient so that drugs and other fluids can be effectively delivered to the patient's vasculature and to break up any fibrin sheath growth.

There are a number of different techniques that have been developed to address the fibrin sheath-impaired venous access catheter. These techniques include new catheter placement, catheter exchange over a guide wire, percutaneous fibrin sheath stripping, and thrombolytic therapy. For example, fibrin sheaths may be removed by mechanical disruption or stripping with a guidewire or loop snare, or by replacing the catheter. Mechanical disruption can help prevent the need to replace the catheter, and thereby eliminate disruption to the patient. However, mechanical disruption may not be effective because the fibrin sheath may not be completely removed and often causes damage to the catheter shaft and vessel wall. Mechanical removal of fibrin build-up may also increase the risk of embolism due to free floating debris within the vessel.

Replacing the catheter is also an option, but this can cause increased trauma to the patient, increased procedure time and costs, increased risks of pulmonary emboli, and may require numerous attempts before removal is successful. Thus, both mechanical disruption and catheter replacement may adversely affect a patient's dialysis schedule, cause patient discomfort, and loss of the original access site. Drug therapies that address the fibrin sheaths can also result in complications and are unreliable.

Therefore, it is desirable to provide a device and method for the destruction of undesirable cellular growth on a venous catheter in a safe, easy, and reliable manner without having to remove the catheter from the patient and without damaging the vein or catheter itself.

SUMMARY OF THE DISCLOSURE

Throughout the present teachings, any and all of the one, two, or more features and/or components disclosed or suggested herein, explicitly or implicitly, may be practiced and/or implemented in any combinations of two, three, or more thereof, whenever and wherever appropriate as understood by one of ordinary skill in the art. The various features and/or components disclosed herein are all illustrative for the underlying concepts, and thus are non-limiting to their actual descriptions. Any means for achieving substantially the same functions are considered as foreseeable alternatives and equivalents, and are thus fully described in writing and fully enabled. The various examples, illustrations, and embodiments described herein are by no means, in any degree or extent, limiting the broadest scopes of the claimed inventions presented herein or in any future applications claiming priority to the instant application.

Disclosed herein are devices for delivering electrical pulses for destruction and/or removal of undesirable cellular growth formations on a venous catheter and methods of using such. In particular, according to the principles of the present invention, an indwelling venous catheter capable of destroying undesirable cellular growth is provided. The catheter includes a shaft having at least one lumen and adapted to be placed inside a vein for long term use. A plurality of electrodes are positioned near the shaft and are adapted to receive from a voltage generator a plurality of electrical pulses in an amount sufficient to cause destruction of cells in the undesirable cellular growth that have grown around the shaft. In one aspect of the invention, a probe is configured to be removably insertable into the at least one lumen and the electrodes are positioned near the distal section of the probe.

BRIEF DESCRIPTION OF THE DRAWINGS

FIG. 1A is a perspective view of an electroporation venous catheter of the current invention with a plurality of electrodes at the distal segment of the catheter.

FIG. 1B is an enlarged cross-sectional view of an electroporation venous catheter taken along line A-A of FIG. 1A showing the arrangement of the electrically conducting elements within the catheter shaft wall.

FIG. 2A is a perspective view showing an electroporation venous catheter of the current invention with electroporation electrodes implanted in the body of a patient.

FIG. 2B is an enlarged view of the distal portion of the catheter of FIG. 1A exhibiting fibrin sheath formation.

FIG. 3A is a partial longitudinal plan view of the distal segment of the electroporation venous catheter showing the arrangement of electrodes and electrically conducting elements.

FIG. 3B is an enlarged cross-sectional view of the electroporation venous catheter taken along line B-B of FIG. 3A showing the attachment between an electrode and an electrically conducting element.

FIG. 7A is an enlarged longitudinal cross-sectional view of an electroporation electrode probe representing yet another embodiment of the current invention.

FIG. 7B is an enlarged longitudinal cross-sectional view of the electroporation electrode probe of FIG. 7A illustrating electrodes in a deployed position.

DETAILED DESCRIPTION OF THE INVENTION

Figure 4:
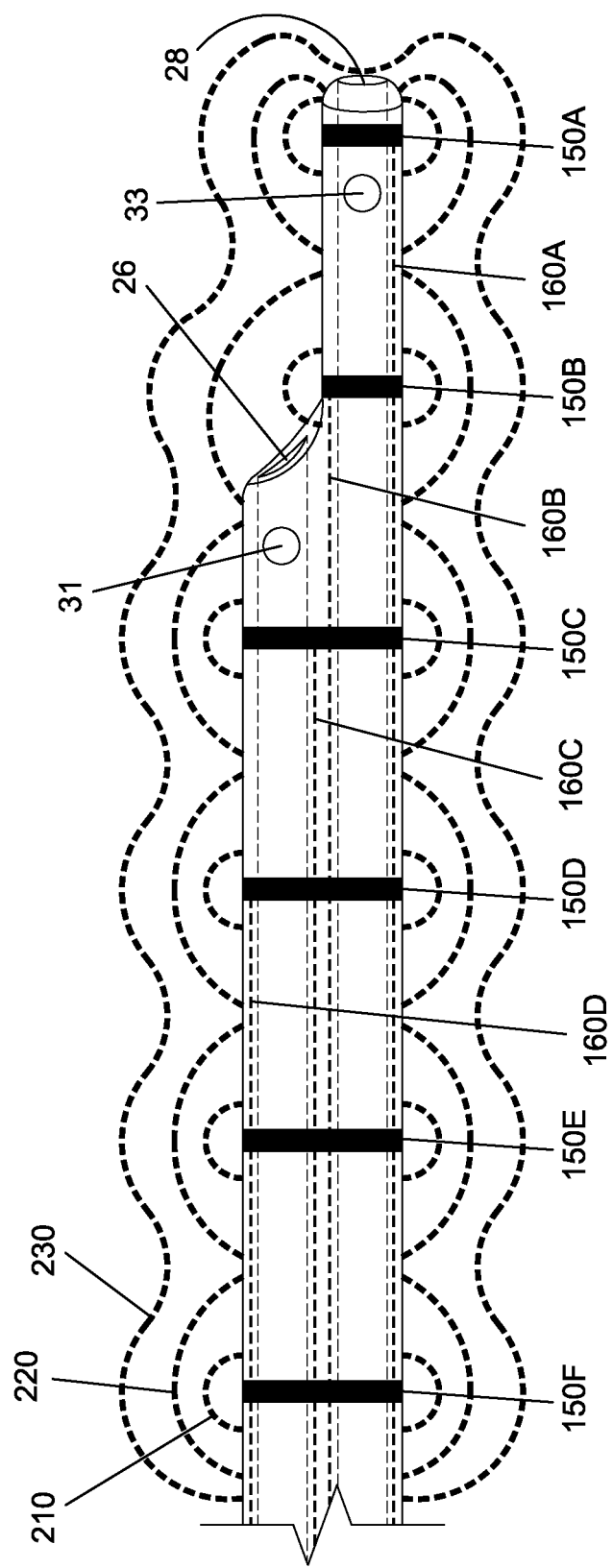
FIG. 4 is a partial plan view of the distal segment of the electroporation venous catheter of FIG. 1A showing the electrical field pattern created when all electrodes are simultaneously energized.

Electroporation is defined as a phenomenon that makes cell membranes permeable by exposing them to certain electric pulses. As a function of the electrical parameters, electroporation pulses can have two different effects on the permeability of the cell membrane. The permeabilization of the cell membrane can be reversible or irreversible as a function of the electrical parameters used. Reversible electroporation is the process by which the cellular membranes are made temporarily permeable. The cell membrane will reseal a certain time after the pulses cease, and the cell will survive. Reversible electroporation is most commonly used for the introduction of therapeutic or genetic material into the cell. Irreversible electroporation, also creates pores in the cell membrane but these pores do not reseal, resulting in cell death.

Irreversible electroporation has recently been discovered as a viable alternative for the ablation of undesired tissue. See, in particular, PCT Application No. PCT/US04/43477, filed Dec. 21, 2004. An important advantage of irreversible electroporation, as described in the above referenced application, is that the undesired tissue is destroyed without creating a thermal effect. When tissue is ablated with thermal effects, not only are the cells destroyed, but the connective structure (tissue scaffold) and the structure of blood vessels are also destroyed, and the proteins are denatured. This thermal mode of damage detrimentally affects the tissue, that is, it destroys the vasculature structure and bile ducts, and produces collateral damage.

Irreversible and reversible electroporation without thermal effect to ablate tissue offers many advantages. One advantage is that it does not result in thermal damage to target tissue or other tissue surrounding the target tissue. Another advantage is that it only ablates cells and does not damage blood vessels or other non-cellular or non-living materials such as implanted medical devices (venous catheters for example).

Fibrin sheaths that form on venous catheters are primarily made up of smooth muscle cells with membranes. Therefore, destruction of the fibrin sheath by irreversible electroporation without causing any thermal effects is a viable method of treating fibrin growth. It is also possible to destroy the cellular structure of fibrin sheath formations using reversible electroporation combined with a drug. This process is known as electroporation-mediated chemotherapy and has been used to introduce chemotherapy drugs into a tumor at an intracellular level. What has not been previously described is the use of electroporation-mediated chemotherapy for the introduction of therapeutic agents, such as cytotoxic agents, into healthy but undesirable tissue such as the smooth muscle cells of a fibrin sheath formation. Cytotoxic agents are transported into the interior of the cell through the transient pore formations, ultimately causing cell death. In this manner, the underlying cellular structure of a fibrin sheath formation can be destroyed by the introduction of cytotoxic agents into the smooth muscles cells comprising the sheath.

Although the following example discusses using the present invention and method to destroy fibrin sheath growth, persons of ordinary skill in the art will appreciate that the present device and method can treat any undesirable cellular growth, including infectious cells.

FIG. 1A illustrates an indwelling electroporation venous catheter 10 with fibrin sheath destruction capabilities. The catheter 10 is comprised of a catheter shaft 25 that extends from a distal end opening 28 to a bifurcate hub 49 and two extension tubes 30, 32. The extension tubes 30, 32 terminate at hub connectors 34, 35 for connection to a dialysis machine. Clamps 41, 42 serve to close off the extension tubes 30, 32 between dialysis sessions. The catheter shaft 25 has at least a first withdrawal lumen 16 and a second supply lumen 18, which share a common internal septum 24, as illustrated in FIG. 1B. First lumen 16 and second lumen 18 extend longitudinally through substantially the entire length of the catheter shaft 25, terminating at distal openings 26 and 28, respectively. Side holes 31 and 33 provide supplemental access to lumens 16 and 18, respectively. FIG. 1B depicts a cross-sectional view of the catheter taken along lines A-A of FIG. 1A illustrating the Double-D lumen shape. Although the cross-sectional lumen configuration shown is a Double-D shape, it is contemplated that lumens 16 and 18 of catheter 10 may have any suitable cross-section lumen shape as required for the particular use of catheter 10.

Catheter 10 includes an electrical connector 500 extending proximally from hub 49 and in the illustrated embodiment positioned between the extension tubes 30 and 32. Catheter 10 also includes a plurality of electrodes 150 attached to the outer surface of the catheter shaft 25. The location of the electrodes on the catheter may be anywhere along the shaft, but the electrodes may generally be located near the distal section of the shaft where the fibrin sheath formation most severely compromises the fluid flow of the device. Furthermore, the size and shape of the electrodes can vary. For example, the electrodes can be ring-shaped, spiral-shaped, or can exist as segmented portions. The electrodes may also be a series of strips placed longitudinally along the catheter shaft surface. The electrodes may be comprised of any suitable electrically conductive material including but not limited to stainless steel, gold, silver and other metals.

A plurality of electrically conducting elements (e.g., electrical wires) 160, shown in FIG. 1B, extend longitudinally within the wall of the catheter shaft and function to connect each electrode 150 to a source of electrical energy in the form of a generator (not shown) by connection through the electrical connector 500. Each electrically conducting element 160 extends from an electrode 150 to which it is connected to terminate in electrical connector 500. An extension cable (not shown) is attached to electrical connector 500 to complete an electrical circuit between the electrodes 150 and the electrical generator through the electrically conducting elements 160. The electrically conducting elements 160 may be comprised of any suitable electrically conductive material including but not limited stainless steel, copper, gold, silver and other metals. The catheter shaft is comprised of a non-conductive material such as urethane, and functions as an electrical insulator insulting each electrically conducting element 160 from the other elements 160 and ensuring that the energy is directed to the exposed electrodes.

FIGS. 2A and 2B illustrate an indwelling electroporation venous catheter 10 of FIG. 1A implanted in the body of a patient 400. Catheter 10 is inserted into vein 404 of a patient 400 with the distal portion of the catheter 10 located at the junction of the superior vena cava 408 and the right atrium of the heart 412, where blood volume and flow rates are maximized. FIG. 2B illustrates fibrin sheath formation 200 attached to the outer wall 25 of the distal segment of catheter 10. As illustrated, the fibrous material occludes the distal end holes 26 and 28 and side holes 31 and 33, thus impairing the functionality of the catheter. Fibrin sheath formation 200 may originate anywhere along the catheter shaft 25 where platelet aggregation begins. For example, fibrin sheath growth 200 may originate at the distal end of the catheter and then develop into a matrix of smooth muscle cells which can block the distal openings 26, 28 and side holes 31 and 33 of the catheter 10.

The electrodes 150 are adapted to administer electrical pulses as necessary in order to reversibly or irreversibly electroporate the cell membranes of the smooth muscle cells comprising the fibrin sheath 200 located along the outer surface of catheter shaft 25 or inside of the catheter shaft 25 within a treatment zone. By varying parameters of voltage, number of electrical pulses and pulse duration, the electrical field will either produce irreversible or reversible electroporation of the cells within the fibrin sheath 200. The pulse generator can be designed to deliver a range of different voltages, currents and duration of pulses as well as number of pulses. Typical ranges include, but are not limited to, a voltage level of between 100-3000 volts, a pulse duration of between 20-200 microseconds (more preferably 50-100 microseconds), and multiple sets of pulses (e.g. 2-5 sets) of about 2-25 pulses per set and between 10 and -500 total pulses. The pulse generator can administer a voltage gradient in a range of from about 2,000 V/cm to about 6,000 V/cm. The pulse generator can deliver pulses which are at a specific known duration and with a specific voltage gradient. For example, the pulse generator can be designed upon activation to provide 10 pulses for 100 microseconds, each pulse providing a voltage gradient of 3,800 V/cm+/−50%+/−25%, +/−10%, or +/−5%. The electroporation treatment zone is defined by mapping the electrical field that is created by the electrical pulses between two electrodes.

When electrical pulses are administered within the irreversible parameter ranges, permanent pore formation occurs in the cellular membrane, resulting in cell death of the smooth muscle cells of the fibrin sheath. In another aspect, by proactively administering the electrical pulses according to a predetermined schedule, fibrin sheath growth 200 on the catheter can be prevented altogether. Alternatively, electrical pulses may be administered within a reversible electroporation range. Cytotoxic drugs, such as a chemotherapy agent, may be administered through either catheter lumen into the volume of fibrin sheath during the electroporation treatment. Temporary pores will form in the cellular membranes of the smooth muscle cells comprising the fibrin sheath, allowing the transport of the drug into the intracellular structure, resulting in cell death.

FIG. 3A illustrates an enlarged partial plan view of the distal segment of the electroporation venous catheter 10 with fibrin sheath removal capabilities. A plurality of electrodes 150 are disposed on the outer surface of the distal portion of the catheter shaft 25. The electrodes 150 are shaped as rings coaxially surrounding the catheter shaft. In this embodiment, each electrode 150 is individually electrically coupled to an electrically conducting element 160. As an example, the distal most electrode 150A is connected to electrically conducting element 160A, which extends within the side wall of the catheter shaft 25 from electrical connector 500 (FIG. 1A) to electrode 150A. Electrically conducting element 160B extends from connector 500 and terminates at electrode

150B. Electrode 150C, as shown, circumferentially surrounds the outer walls of both lumens 16 and 18 and is electrically coupled to electrically conducting element 160C which terminates in the catheter side wall at the location of electrode 150C. Similarly, electrode 150D, 150E and 150F are electrically coupled to conducting elements 160D, 160E and 160F respectively.

FIG. 3B depicts an enlarged cross-sectional view of catheter 10 taken along lines B-B of FIG. 3A at the location of electrode 150D. Catheter shaft 25 is comprised of lumens 16 and 18 separated by a septum 24. Coaxially surrounding shaft 25 is ring electrode 150D. Electrically conducting elements 160A, 160B, 160C and 160D are also illustrated embedded within the catheter shaft 25 wall. The catheter shaft 25 is comprised of a non-conductive urethane material and functions as an electrical insulator insulating each electrically conducting element from the other elements and from those electrodes 150 not physically coupled to the conducting element. Electrically conducting element 160D is shown in FIG. 3B as being electrically coupled to electrode 150D by an electrically conductive material 320. To create the coupling, the catheter shaft 25 surface may be skived until the outer surface of the coupling wire 160D is exposed. This process creates skive pocket 310. Pocket 310 is filled with electrically conductive material 320 to create an electrically conductive pathway between electrode 150D and electrically conducting element 160D.

Other methods known in the art for electrically coupling the electrodes 150 and electrically conducting elements 160 are within the scope of this invention. Examples of coupling methods include spot welding the electrode 150 to the conducting element 160, soldering and mechanical crimping, among other techniques. Other electrically conducting element configurations are also within the scope of this invention. For manufacturing efficiencies, for example, shaft 25 may be extruded with all electrically conducting elements 160 embedded in the shaft for substantially the entire length of the catheter shaft 25. Only the electrode 150 to which the conducting element 160 is coupled will be activated when the electrical circuit is energized. Those segments of the electrically coupling elements 160 distal of the electrode 150 connection will not generate an electrical field of sufficient intensity to induce a clinical effect when activated since they are not connected to any other electrodes.

FIG. 4 depicts the electrical field pattern created when electrical pulses are applied to the catheter 10 shown in FIG. 3A. In the embodiment shown, electrical pulses may be simultaneously applied to all electrodes 150A-150F with alternating polarity. As an example, electrode 150F may have a positive polarity, electrode 150E a negative polarity, electrode 150D a positive polarity, electrode 150C a negative polarity, electrode 150B a positive polarity and electrode 150A a negative polarity. This arrangement creates the electrical field pattern illustrated by field gradient lines 210, 220 and 230. The voltage pulse generator (not shown) is configured to generate electrical pulses between electrodes in an amount which is sufficient to induce irreversible electroporation of fibrin sheath smooth muscle cells without creating a clinically significant thermal effect to the treatment site. Specifically, the electrical pulses will create permanent openings in the smooth muscles cells comprising the fibrin sheath, thereby invoking cell death without creating a clinically significant thermal effect. The smooth muscle cells will remain in situ and are subsequently removed by natural body processes.

The strongest (defined as volts/cm) electrical field is nearest to the electrodes 150 and is depicted by gradient line 210 in FIG. 4. As the distance away from the electrode 150 increases, the strength of the electrical field decreases. Gradient line 230 represents the outer perimeter of irreversible electroporation effect and as such defines the outer boundary of cell kill zone. As an example, any fibrin or other bio-film growth on the surface of the catheter within the outer perimeter 230 will undergo cell death by irreversible electroporation.

Because the voltage pulse generation pattern from the generator does not generate damaging thermal effect, and because the voltage pulses only ablate living cells, the treatment does not damage blood, blood vessels or other non-cellular or non-living materials such as the venous catheter itself.

Figure 5:
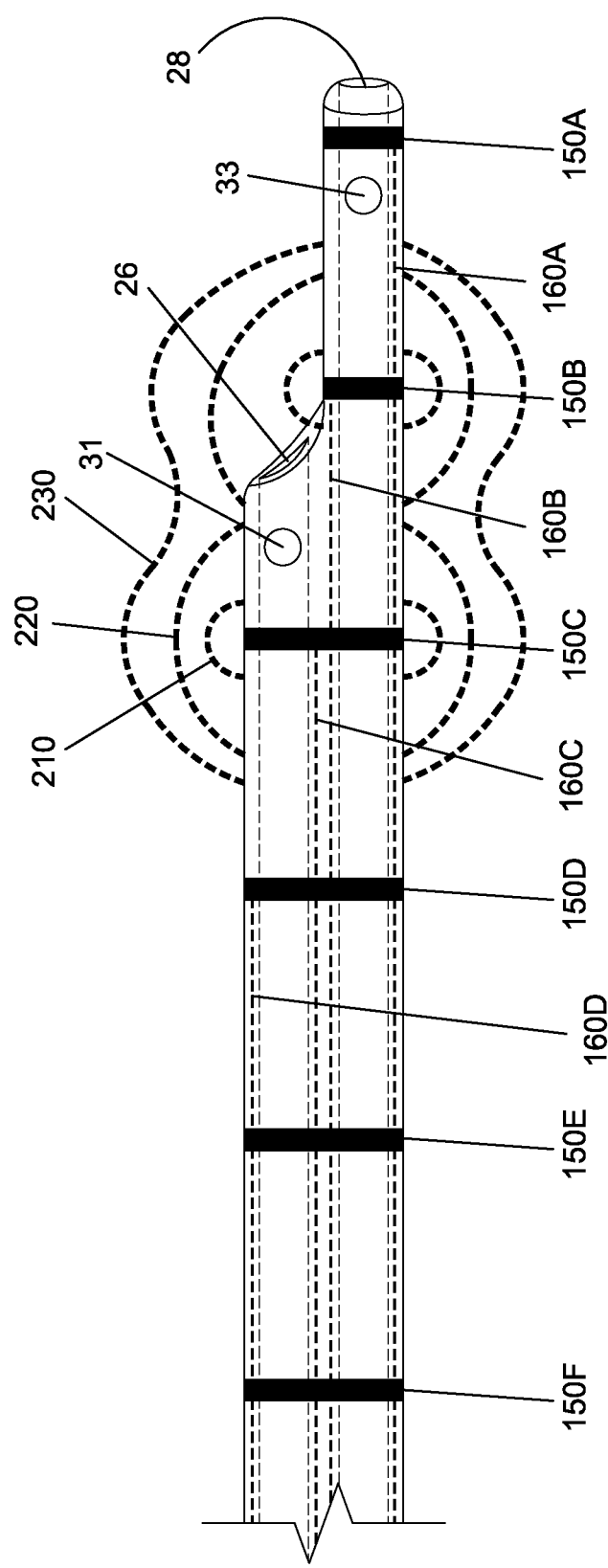
FIG. 5 is a partial longitudinal view of the distal segment of the electroporation venous catheter showing the electrical field pattern created when only two electrodes are energized.

By utilizing separate electrically conducting elements 160 for each electrode 150, different fibrin sheath growth 200 segments may be treated independently. For example, a computer (not shown) within the generator can control the firing of each electrode pair independently and according to a predetermined pattern. Alternatively, the creation of a series of electrical fields may be accomplished by sequentially firing pairs of electrodes within one treatment session to ensure that the entire length of the fibrin sheath is treated. Sequentially polarizing and applying electrical energy to a subset of the total number of electrodes as described herein may be used to target fibrin growth on a specific segment of the catheter shaft. As an example, FIG. 5 depicts the electrical fields created when electrical pulses are applied to two electrodes only. Electrode 150B may be set to have a positive polarity and electrode 150C a negative polarity. When electrical pulses are applied to these two electrodes, an electrical field pattern is created as illustrated by gradient lines 210, 220 and 230. Fibrin sheath build-up within the outer perimeter of gradient line 230 will be effectively destroyed.

In another aspect of the invention, the device and method can be used to cause the destruction of infectious cells, such as catheter-related bacteremia, that have grown around the indwelling catheter. These infectious cells can be located anywhere along the indwelling shaft. Research has also shown that infectious cells can form in combination with fibrin sheath growths, because fibrin sheath can enhance catheter-related bacteremia by providing an interface for adherence and colonization. These pathogens may then produce a "biofilm" which is impenetrable to systemic antibiotics leading to a cause of catheter dysfunction, subsequent removal, and the attendant increase in morbidity and mortality. Referring again to FIG. 4, the pulse parameters that characterize the field gradient line can be adjusted to vary the treatment zone according to the location of the fibrin sheath growth and/or infectious cells to be destroyed. Furthermore, in some embodiments of the invention, the electrodes can be positioned at any location necessary to destroy any such infectious cells that have grown around the indwelling catheter. For example, the electrodes can be positioned at a proximal section of the indwelling catheter for treating infectious cells that have grown around the tunneled portion of the catheter. In addition, the electrodes can be positioned to destroy infectious cells that have grown near the insertion site of the indwelling catheter.

In another aspect of the invention, by periodically administering the electrical pulses according to a predetermined schedule, fibrin sheath growth on the catheter shaft 20 can be prevented altogether. As an example, the formation of a fibrin sheath may occur as early as 24 hours after catheter implantation. Smooth muscle cells develop within seven days. Application of electrical pulses applied to fibrin sheath at regular intervals post-implantation may be effective in preventing fibrin sheath growth during the catheter implantation period.

Figure 6A:
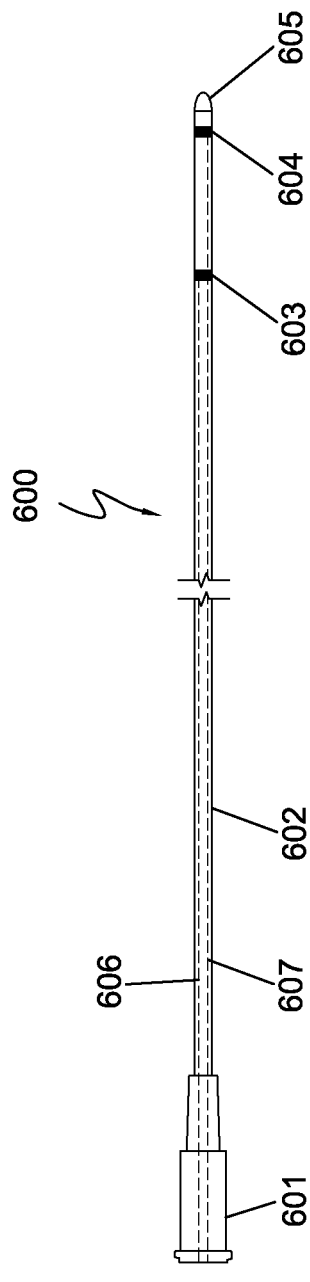
FIG. 6A is a plan view of an electroporation electrode probe representing another embodiment of the current invention.
Figure 6B:
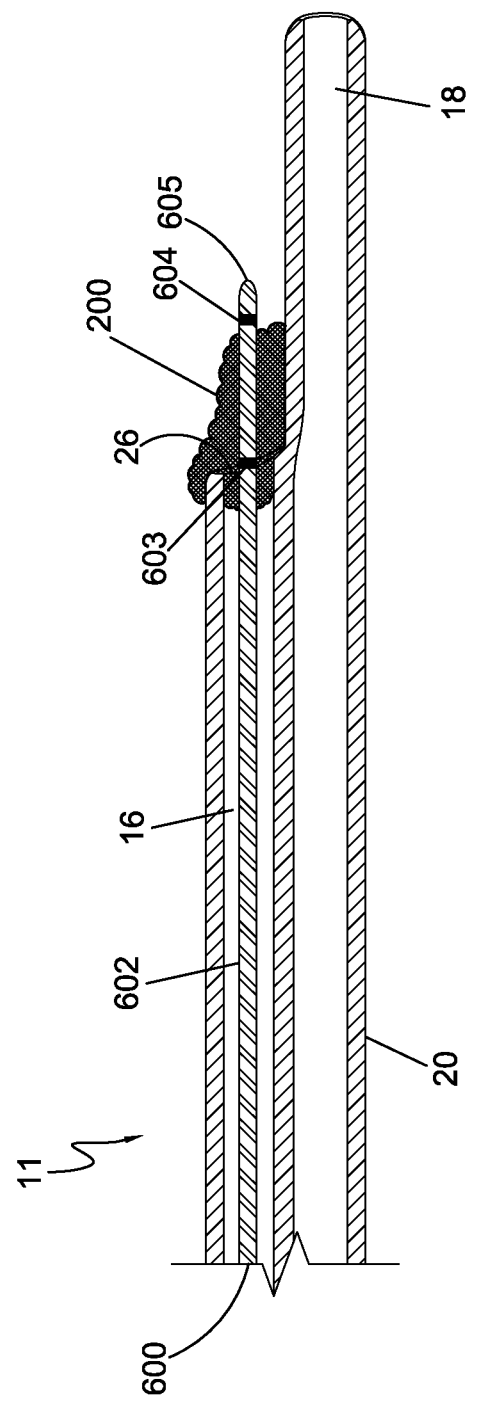
FIG. 6B is a partial longitudinal cross-sectional view of the distal segment of a venous catheter with the electroporation electrode probe of FIG. 6A inserted through the catheter lumen and positioned within a fibrin sheath formation.

Referring now to FIG. 6A and 6B, FIG. 6A is a plan view of an electroporation probe 600 representing another embodiment of the current invention. In this embodiment an electroporation probe 600 is comprised of an electrical connector 601, a flexible shaft body 602 on which two electrodes 603 and 604 are positioned in a coaxial arrangement with the shaft, and a distal end or tip 605. The electrodes are preferably positioned near a distal section of the shaft. As previously described electrically conductive elements 606 and 607 extend longitudinally from the electrical connector 601 to the electrodes 603 and electrode 604 respectively. The electrically conductive elements 606 and 607 may be embedded within the wall of the shaft 602, as previously described, or alternatively may be insulated and positioned within a lumen of shaft 602.

FIG. 6B is a partial longitudinal cross-sectional view of the distal segment of a venous catheter 11 with the distal section of electrode probe 600 of FIG. 6A inserted through the catheter lumen 16 and positioned within a fibrin sheath formation 200. To destroy the fibrin sheath 200, the electrode probe 600 is inserted into the catheter lumen 16 and advanced through the distal end hole 26. Electrode probe distal tip 605 may be tapered to provide a non-traumatic leading edge capable of advancing through the sheath formation 200. Electrodes 603 and 604 are positioned within the fibrin sheath formation 200 such that when electrical pulses are applied, an electrical field (not shown) will be created that encompasses the fibrin sheath 200 in its entirety. After the electroporation process has destroyed the fibrin sheath, the probe is removed from the catheter. Alternatively, cytotoxic agents may be administered through lumen 16 and directed into the fibrin formation. Electroporation pulses may be applied to reversibly electroporate the smooth muscle cells of sheath 200, creating a pathway through the cell membrane for the agent to enter the cell.

The embodiment illustrated in FIG. 6A and 6B is particularly advantageous when treating a fibrin sheath formation that has advanced into the lumen of the catheter and occludes the end holes and/or side holes of the catheter. Another advantage of the embodiment of FIG. 6A is that the probe is a separate device inserted into the patient through the implanted catheter only when treatment is required and then is removed immediately after treatment. The probe is not part of the implanted catheter device and is removed immediately after treatment. Utilizing a separate device to perform electroporation reduces the possibility of electrode or conducting wire damage due to long term implantation as well as simplifying the manufacturing of the device and costs associated with the manufacture.

Figure 7C:
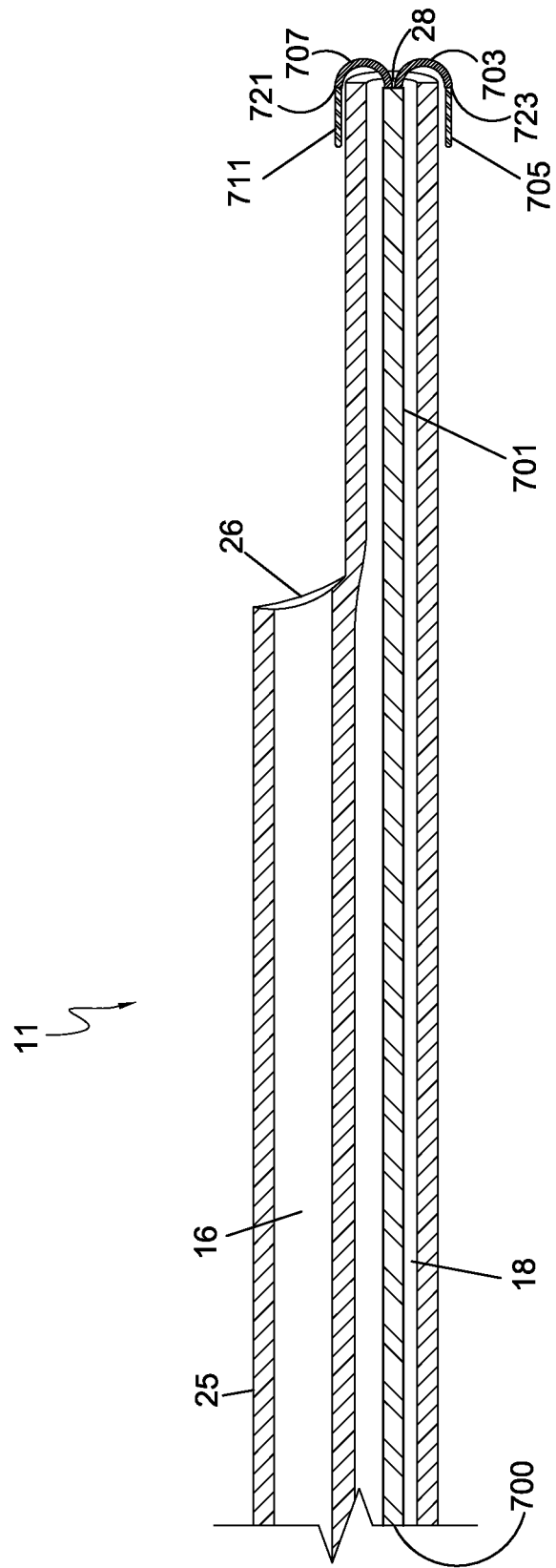
FIG. 7C is a partial longitudinal cross-sectional view of the distal segment of a venous catheter with the electroporation electrode probe of FIG. 7A inserted through the catheter lumen with deployed electrodes positioned around the distal segment of the catheter.

FIGS. 7A-7C illustrate a third embodiment of the present invention wherein the electroporation probe 700 is comprised of deployable electrodes. As with the previous embodiment, the electroporation probe 700 is inserted into the lumen of a catheter prior to the application of electrical pulses, and is removed after treatment. Referring first to FIG. 7A, electrode probe 700 is comprised of an electrical connector hub 712, an outer sheath 701 extending from the hub 712 to a distal end hole 702, and a plurality of electrically conducting elements 709 and 704 arranged within the outer sheath 701 and within a lumen. Electrically conducting elements 709 and 704 are connected proximally to the electrical connector/hub 712 and extend distally within the outer sheath 701 for substantially the entire length of the sheath. Insulating sleeves 707 and 703 coaxially surround electrically conducting elements 709 and 704 from the hub 712 to insulation distal ends 721 and 723. Un-insulated portions 711 and 705 of electrically conducting elements 709 and 704 extend distally. Portions 711 and 705, being un-insulated, act as electrodes when the electrical circuit is energized.

Button 713 on hub 712 is used to deploy and retract the electrically conducting elements 709 and 704 relative to the outer sheath 701. The undeployed position of electroporation probe 700 is illustrated in FIG. 7A. As shown, the electrically conducting elements 709 and 704 are completely contained within the lumen of the outer sheath 701 including the un-insulated portions 711 and 705. The fully deployed position of the electrode probe 700 is illustrated in FIG. 7B. Button 713 is advanced distally to deploy the distal sections of electrically conducting element 709 and 704 out of the distal end hole 702 of outer sheath 701. When fully deployed, the distal section of the electrically conducting elements 709 and 704 extend outwardly from end hole 702, with a profile that curves outwardly and then extends proximally in a substantially parallel relationship with the longitudinal axis of the probe 700. The distal portion of insulating sleeves 707 and 703 form at least part of the curve terminating at points 721 and 723. The un-insulated portions 711 and 705 form the active electrodes and extend from insulation end points 721 and 723 in a proximal direction adjacent (such as parallel to) the outer wall of outer sheath 701.

Electrically conductive elements 704 and 709 may be formed of any suitable electrically conductive material including but not limited stainless steel, gold, silver and other metals including shape-memory materials such as nitinol. Nitinol is an alloy with super-elastic characteristics which enables it to return to a pre-determined expanded shape upon release from a constrained position. The outer sheath 701 constrains the distal segments of the undeployed electrically conductive elements 704 and 709 in a substantially straight distal configuration. Once the electrodes are deployed from the distal end of the outer sheath 701 as previously described, the distal sections of electrically conductive elements 704 and 709 form the "J-hook" curved profile shown in FIG. 7B.

FIG. 7C illustrates a partial longitudinal cross-sectional view of a catheter 11 with the electrode probe 700 in a deployed position. In use, the undeployed electrode probe 700 is inserted into lumen 18 of catheter 11 and advanced to the distal end hole 28. Once correctly positioned, button 713 (shown in FIG. 7B) is advanced in the direction shown by the hub arrow to deploy the distal sections of electrically conducting elements 709 and 704 outside of the outer sheath 701 and the catheter distal end hole 28. When fully deployed, the exposed segments 711 and 705 of electrically conducting elements 709 and 704 extend in a proximal direction adjacent to and parallel to the outer wall of catheter shaft 25.

Figure 8:
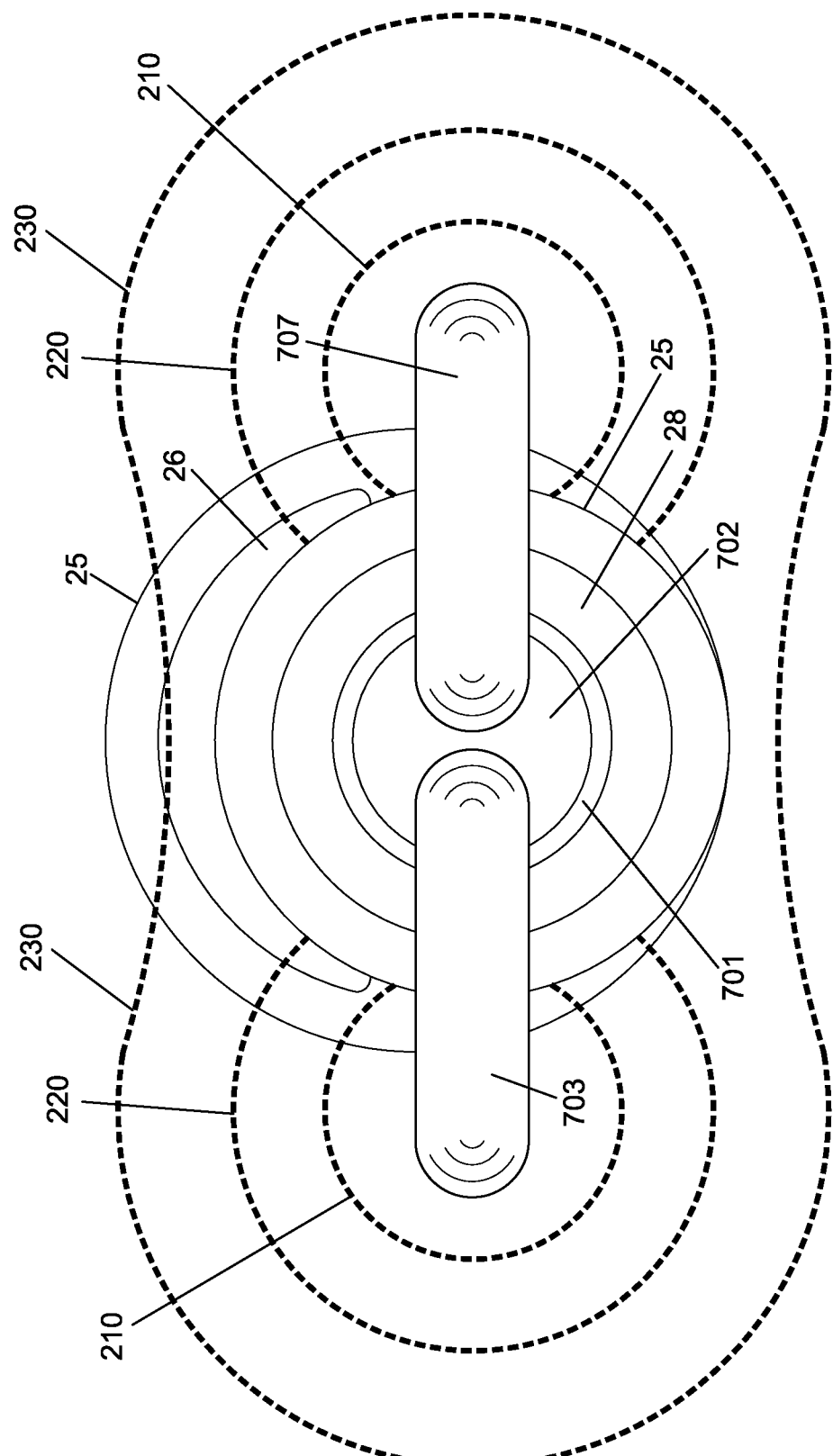
FIG. 8 is a distal end view of the venous catheter shown in FIG. 7C illustrating the electrical field pattern created when the deployed electrodes are energized.

FIG. 8 is an enlarged end view of the catheter of FIG. 7C depicting the electrical fields created when electrical pulses are applied to electrode probe 700. Application of pulses creates an electrical field pattern between the un-insulated portions 711 and 705 (shown in FIG. 7C) of the electrically conducting elements. This arrangement creates the electrical field pattern illustrated by field gradient lines 210, 220 and 230. The strongest (defined as volts/cm) electrical field is nearest to the active electrodes and is depicted by gradient line 210. As the distance away from the electrodes increase, the strength of the electrical field decreases. Gradient line 230 represents the outer perimeter of irreversible electroporation effect and as such defines the outer boundary of cell kill zone. As an example, any fibrin or other bio-film growth on the surface of the catheter within the outer perimeter 230 will undergo cell death by irreversible electroporation.

If fibrin sheath has formed around end hole 26, electrode probe 700 may be inserted into lumen 16 (shown in FIG. 7C), positioned and then electrodes deployed as previously described. Application of electrical pulses will create an electrical field as shown in FIG. 8, except the field will be centered around end hole 26 rather than end hole 28. It is also within the scope of this invention to utilize two electrode probes of opposite polarity with one probe placed in each lumen. In this embodiment, the electrical field may be created between the two probes, creating an electrical field similar to that illustrated in FIG. 4.

The deploying electrode probe 700 illustrated in FIGS. 7A-C and 8 is particularly advantageous in destroying fibrin build-up along the outer surface of the distal segment of an implanted catheter. Probe 700 may be used to clear fibrin sheath formations from each lumen of a catheter as well as to irreversibly electroporate fibrin sheath occluding side holes located near the distal end of the catheter. The number of electrically conducting elements 704 and 709 may be varied to accommodate various size catheters and fibrin sheath volumes. In addition, the length of the exposed segment 711 and 705 may be adjusted based on the catheter length and/or the length of the fibrin formation extending proximally from the distal end holes of the catheter. It is also within the scope of this invention to configure a probe with two deployable electrodes which, when deployed, are arranged at an angle relative to each other of less than 180 degrees (i.e., not parallel to each other). After applying electrical pulses to create an electrical field pattern, the probe may be rotated and pulse applied again to create a second electrical field pattern. This process is repeated until the entire 360 degree circumference of the outer surface of the catheter has been treated. It is also understood that any of the embodiments illustrated may be used to reversibly electroporate the fibrin sheath for the purpose of introducing therapeutic agents into the smooth muscle cells.

Figure 9:
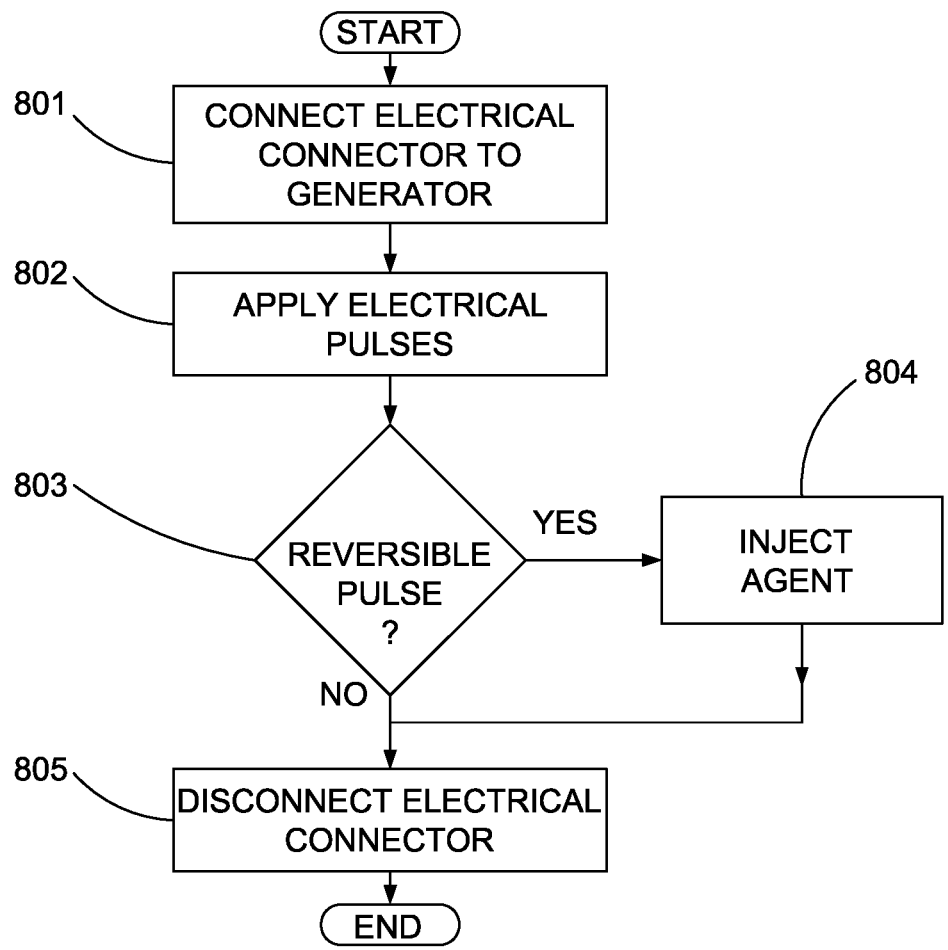
FIG. 9 is a flowchart depicting the method steps for fibrin sheath destruction using the electroporation catheter of FIG. 1A.

FIG. 9 illustrates the procedural steps associated with performing irreversible or reversible electroporation treatment using the device which is depicted in FIGS. 1-5. After the fibrin sheath formation has been detected and the location of the formation determined using ultrasound or fluoroscopic imaging, electrical connector 500 is connected to an electrical generator (801) using an extension cable. This completes an electrical circuit between the electrodes 150 and the generator via the electrically conducting elements 160. Electrical pulses are applied across the electrodes in the desired pattern to electroporate the smooth muscle cells of the fibrin sheath (802). If the electrical generator treatment parameters are set to deliver electrical pulses within the reversible range (803), therapeutic agents may be injected through the catheter lumens (804) and pass into the fibrin sheath formation through either the side holes or end holes of the catheter. After treatment, the extension cable is disconnected from the electrical connector (805). Non-thermal death of the smooth muscle cells will occur within the first twenty-four hours after electroporation treatment followed by a cellular breakdown of the fibrin sheath.

Figure 10:
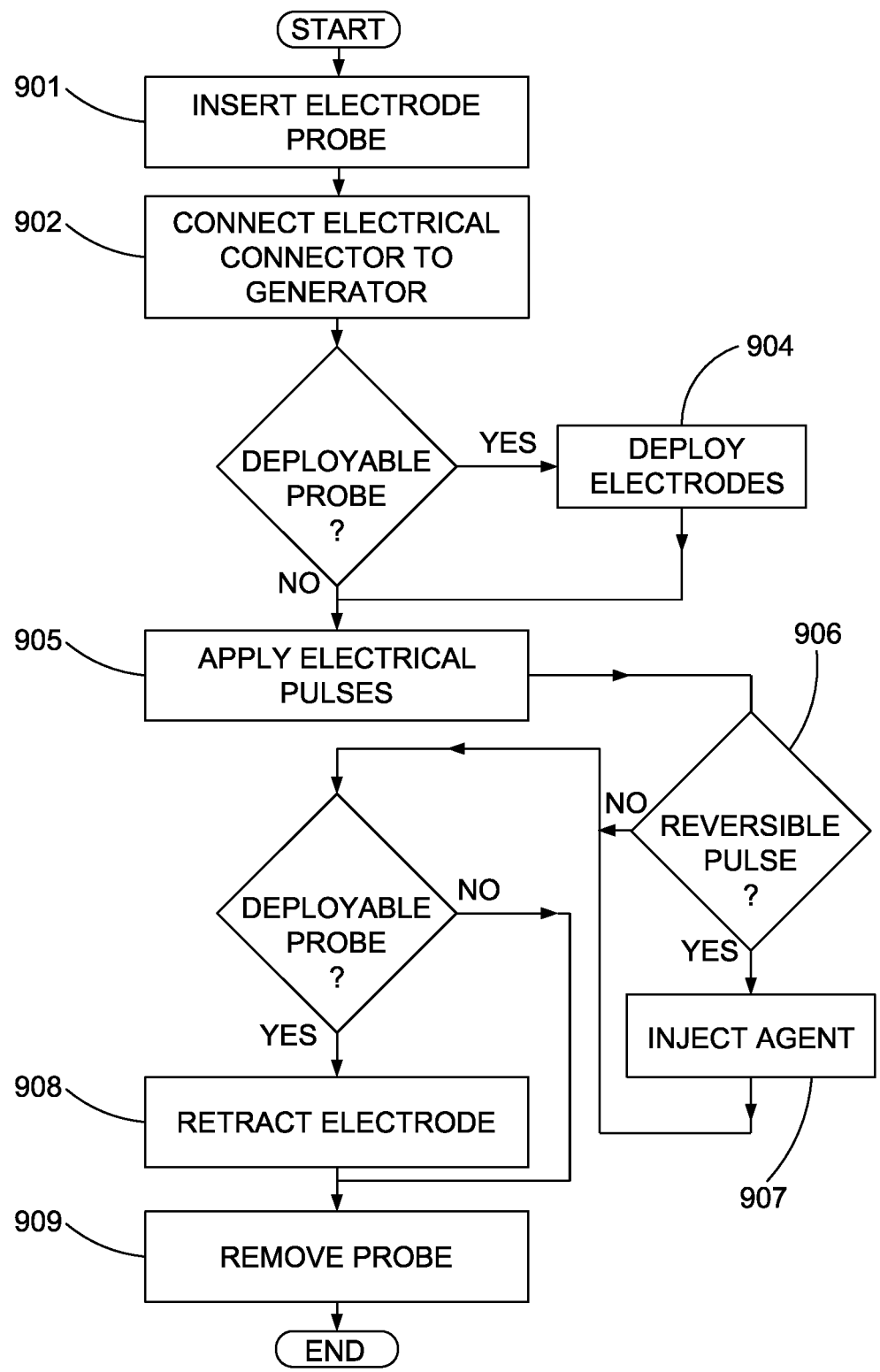
FIG. 10 is a flowchart depicting the method steps for fibrin sheath removal using the electroporation electrode probe of FIG. 6A or 7A.

Referring now to FIG. 10, the method of performing electroporation treatment using the device depicting in FIGS. 6A-B or FIG. 7A-C is illustrated. After the fibrin sheath formation has been detected and the location of the formation determined using ultrasound or fluoroscopic imaging, electrode probe 600 (FIGS. 6A-B) or 700 (FIGS. 7A-C) is inserted into the venous catheter (901). The probe is then positioned relative to the fibrin sheath location as previously described. The electrical connector 601 or 712 is then connected to an electrical generator using an extension cable (902). If using electrode probe 700, the electrodes are deployed (904) and positioned outside of the catheter shaft as shown in FIG. 7C. Electrical pulses are then applied across the electrodes (905) creating a field gradient sufficient to non-thermally electroporate the smooth muscle cells present in the fibrin sheath. If the electrical generator treatment parameters are set to deliver electrical pulses within the reversible range (906), therapeutic agents may be injected through the catheter lumen (907) passing into the fibrin sheath formation through either the side holes or end holes of the catheter. Alternatively, the electroporation probe may be configured to include a lumen through which agents may be administered. If using probe 700, the electrodes are then retracted (908) within the outer sheath 701. After the procedure is complete, the probe is removed from the catheter (909). Non-thermal death of the smooth muscle cells occur after electroporation treatment followed by a cellular breakdown of the fibrin sheath.

Figure 11:
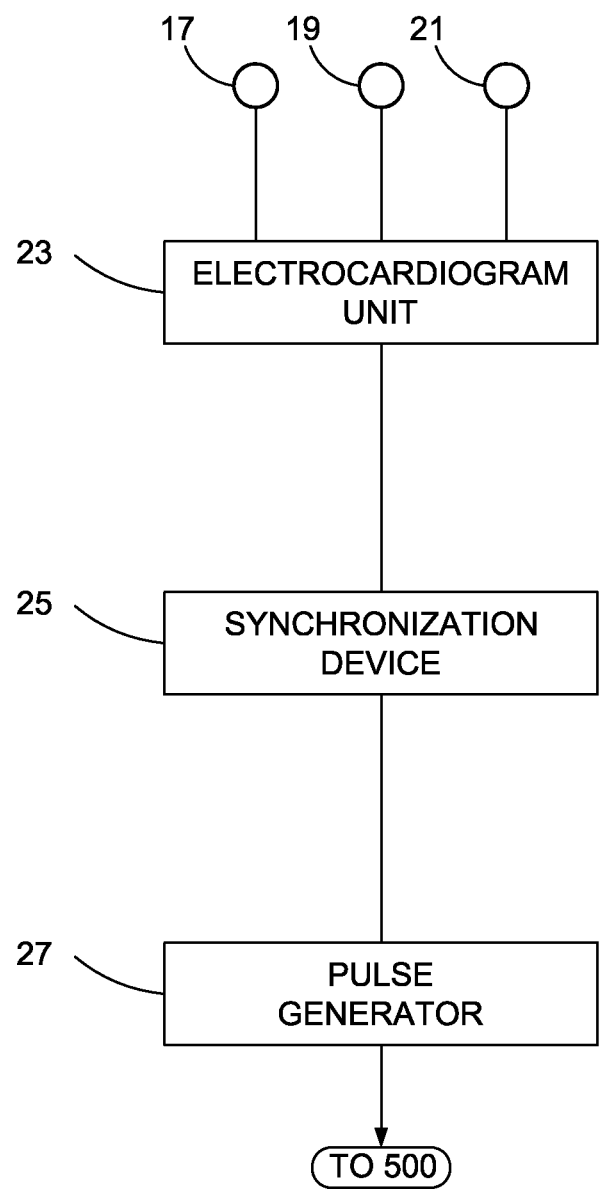
FIG. 11 is a treatment setup for a patient for synchronization of the delivery of electroporation pulses with a specific portion of the cardiac rhythm.

In one embodiment, the electroporation pulses can be synchronously matched to specifically repeatable phases of the cardiac cycle to protect cardiac cellular functioning. See, for example, U.S. Patent pplication No. 61/181,727, filed May 28, 2009, entitled "Algorithm For Synchronizing Energy Delivery To The Cardiac Rhythm", which is fully incorporated by reference herein. This feature is especially useful when the electroporation pulses are delivered in a location that is near the heart. FIG. 11 illustrates a treatment setup for a patient for synchronization of the delivery of electroporation pulses with a specific portion of the cardiac rhythm. Electrocardiogram (ECG) leads 17, 19, 21 are adapted to be attached to the patient for receiving electrical signals which are generated by the patient's cardiac cycle. The ECG leads transmit the ECG electrical signals to an electrocardiogram unit 23. The electrocardiogram unit 23 can transmit this information to a synchronization device 25 which can include hardware or software to interpret ECG data. If the synchronization device 25 determines that it is safe to deliver electroporation pulses, it sends a control signal to a pulse generator 27. The pulse generator 27 is adapted to connect to electrical connector 500 for delivering electroporation pulses. Each of the synchronization device 25 and pulse generator 27 can be implemented in a computer so that they can be programmed.

The present invention affords several advantages. Fibrin sheath growths are destroyed without having to remove the catheter from the patient. The treatment is minimally-invasive and highly efficacious. Because irreversible electroporation does not create thermal activity, the catheter is not damaged by the treatment. Fibrin sheath growths are treated quickly, and the catheters can be maintained according to a predetermined schedule to insure that the distal openings remain clear.

Although the irreversible electroporation device and method has been described herein for use with dual-lumen catheters, it should be understood that the irreversible electroporation device can be used with single lumen catheters or multiple-lumen catheters. Another type of venous catheter which is prone to fibrin sheath formation is a venous catheter that is connected to an implanted port. An example of a venous catheter attached to an implanted port is disclosed in U.S. Pat. Application Publication No. 2007/0078391, which is incorporated herein by reference. Electrode probe devices described in FIGS. 6A-B and 7A-C may be used to remove fibrin sheath from catheter shafts connected to implanted port devices. In the case of port devices, the probe may be inserted through a needle lumen that has been inserted into the septum. The probe device may include a guidewire lumen to assist in tracking through the stem channel and into the catheter shaft lumen. Fibrin sheath formations on PICC lines or other central venous catheters may also be destroyed using the devices and methods illustrated herein.

While the embodiments shown use pulses that cause IRE, persons of ordinary skill in the art will appreciate that other types of pulses can be used for the destruction of the fibrin sheath growths. In particular, ultrashort sub-microsecond pulses (pulses of less than 1 microsecond in duration) can be used to induce apoptosis that cause damage to the intracellular structures such as a cell nucleus.

The above disclosure is intended to be illustrative and not exhaustive. This description will suggest many modifications, variations, and alternatives may be made by ordinary skill in this art without departing from the scope of the invention. Those familiar with the art may recognize other equivalents to the specific embodiments described herein. Accordingly, the scope of the invention is not limited to the foregoing specification.

What is claimed is:

1. A method of treating undesirable cellular growth on an indwelling venous catheter comprising:
   connecting a voltage generator to a plurality of electrodes that are positioned on a shaft of the indwelling venous catheter;
   applying a predetermined schedule of electrical pulses generated by the voltage generator between the plurality of connected electrodes while the shaft of the indwelling venous catheter is positioned inside a vessel the predetermined schedule of electrical pulses being of an amount sufficient to prevent the undesirable cellular growth around the shaft of the indwelling venous catheter and to electroporate cells of the undesirable cellular growth that may have formed around the shaft of the indwelling venous catheter; and
   introducing a therapeutic agent into the electroporated cells of the undesirable cellular growth;
   wherein the therapeutic. agent is formulated to cause cell death in the electroporated cells.

2. The method of claim 1, further comprising:
   receiving electrocardiogram (ECG) signals from a synchronization device, wherein generation of the electrical pulses by the voltage generator is based on the received ECG signals.

3. The method of claim 1, wherein the therapeutic drug is a cytotoxic agent.

4. The method of claim 1, wherein the plurality of electrodes are ring shaped and located near a distal end of the indwelling venous catheter.

5. The method of claim 1, wherein the plurality of electrodes are spiral shaped and located as segmented portions along a distal end of the indwelling venous catheter.

6. The method of claim 1, wherein the predetermined schedule of electrical pulses is sufficient to cause permanent pore formation in the cellular membrane of the undesirable cellular growth around the shaft of the indwelling venous catheter.

7. The method of claim 1, wherein the indwelling venous catheter further comprises an electrical concluding element and a surface of the indwelling venous catheter has skives or pockets filled with electrically conductive material.

8. The method of claim 1, wherein the predetermined schedule of electrical pulses are simultaneously applied to all of the plurality of connected electrodes with alternating polarity.

9. The method of claim 1, wherein the predetermined schedule of electrical pulses creates permanent openings in the undesirable cellular growth without creating a significant thermal effect to the undesirable cellular growth.

10. The method of claim 9, wherein the undesirable cellular growth contains at least smooth muscle cells that will remain after the predetermined schedule of electrical pulses and will be removed by natural body processes.

* * * * *